US008236951B2

(12) United States Patent
Hanson et al.

(10) Patent No.: US 8,236,951 B2
(45) Date of Patent: Aug. 7, 2012

(54) THIOXANTHINE DERIVATIVES AS MYELOPEROXIDASE INHIBITORS

(75) Inventors: Sverker Hanson, Sodertalje (SE); Gunnar Nordvall, Sodertalje (SE); Anna-Karin Tiden, Sodertalje (SE)

(73) Assignee: AstraZeneca AB, Sodertalje (SE)

(*) Notice: Subject to any disclaimer, the term of this patent is extended or adjusted under 35 U.S.C. 154(b) by 31 days.

(21) Appl. No.: 12/185,158

(22) Filed: Aug. 4, 2008

(65) Prior Publication Data
US 2008/0293748 A1 Nov. 27, 2008

Related U.S. Application Data

(63) Continuation of application No. 10/511,537, filed as application No. PCT/SE03/00617 on Apr. 15, 2003, now Pat. No. 7,425,560.

(30) Foreign Application Priority Data

Apr. 19, 2002 (SE) ..................... 0201193
Jul. 17, 2002 (SE) ..................... 0202239

(51) Int. Cl.
C07D 473/22 (2006.01)
A61K 31/522 (2006.01)
A61P 29/00 (2006.01)
A61P 9/10 (2006.01)
A61P 25/28 (2006.01)

(52) U.S. Cl. ......... 544/267; 544/311; 544/310; 544/123
(58) Field of Classification Search .......... 544/118, 544/267, 273, 270, 269; 514/234.2, 263.2, 514/263.23, 263.34, 263.36
See application file for complete search history.

(56) References Cited

U.S. PATENT DOCUMENTS

| 3,135,753 | A | * | 6/1964 | Hitchings et al. ............. 544/265 |
| 4,710,503 | A | | 12/1987 | Hofer |
| 4,820,709 | A | | 4/1989 | Hofer |
| 5,173,491 | A | | 12/1992 | Kamoun et al. |
| 5,453,426 | A | | 9/1995 | Jacobson et al. |
| 5,489,598 | A | | 2/1996 | Connor et al. |
| 5,716,967 | A | | 2/1998 | Kleinman |
| 5,756,511 | A | | 5/1998 | West et al. |
| 5,976,823 | A | | 11/1999 | Wu |
| 6,025,361 | A | * | 2/2000 | Cavalla et al. ............ 514/263.34 |
| 6,046,019 | A | | 4/2000 | Goumeniouk et al. |
| 6,066,641 | A | * | 5/2000 | Cavalla et al. ............ 514/263.21 |
| 6,294,541 | B1 | | 9/2001 | Cavalla et al. |
| 6,319,928 | B1 | * | 11/2001 | Chasin et al. ............ 514/263.22 |
| 7,108,997 | B2 | | 9/2006 | Kettle |
| 7,425,560 | B2 | * | 9/2008 | Tiden ................. 514/263.34 |
| 2004/0022871 | A1 | | 2/2004 | Mainnemare |
| 2004/0029871 | A1 | | 2/2004 | Kettle et al. |
| 2005/0070558 | A1 | | 3/2005 | Vidal Juan et al. |
| 2007/0032468 | A1 | | 2/2007 | Kettle et al. |
| 2007/0093483 | A1 | | 4/2007 | Svensson et al. |
| 2008/0221133 | A1 | | 9/2008 | Tiden |
| 2008/0312311 | A1 | * | 12/2008 | Aslund et al. ............... 514/437 |
| 2009/0054468 | A1 | * | 2/2009 | Eriksson et al. ......... 514/263.21 |
| 2009/0149475 | A1 | * | 6/2009 | Tiden et al. .............. 514/255.05 |

FOREIGN PATENT DOCUMENTS

| CN | 1013676 B | 8/1991 |
| EP | 0010531 B1 | 4/1980 |
| EP | 0359505 | 3/1990 |
| EP | 0430300 | 6/1991 |
| EP | 0452926 | 3/1996 |
| EP | 1016407 | 7/2000 |
| JP | 02160235 | 6/1990 |
| WO | 8906125 | 7/1989 |
| WO | 9101730 | 2/1991 |
| WO | 95/00516 A1 | 1/1995 |

(Continued)

OTHER PUBLICATIONS

Garst, G. L. Kramer, Y. J. Wu, and J. N. Wells, J. Med. Chem.; 1976; 19(4) pp. 499-503.* van Galen et al. Mol Pharmacol 45 (6): 1101 (1994).*
Peter W. K. Woo, et al., J. Med. Chem.; 1992; 35(8) pp. 1451-1457.*
Armitage et al., British Journal of Pharmacology and Chemotherapy (1961), 17, 196-207.*
CAPLUS 1986:626214, English abstract for CN 1013676.
Non-final Office Action issued for U.S. Appl. No. 10/476,999 on Oct. 31, 2005 (U.S. Appl. No. 10/476,999 issued Sep. 19, 2006 as U.S. patent No. 7,108,997, which was cited on Form SB08a submitted Jul. 23, 2007).
Advisory Action issued for U.S. Appl. No. 10/275,824 on May 22, 2007 (U.S. Appl. No.10/275,824, which is now abandoned, published as U.S. publication No. 2004-0029871, which is cited hereinabove).

(Continued)

Primary Examiner — Mark L Berch
(74) Attorney, Agent, or Firm — David Gryte

(57) ABSTRACT

There is disclosed the use of a compound of formula (Ia) or (Ib)

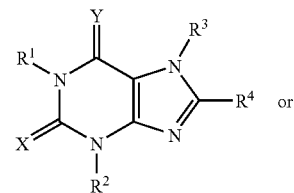

(Ia)

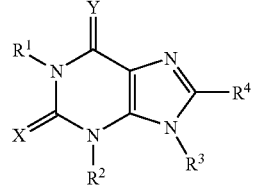

(Ib)

wherein $R^1$, $R^2$, $R^3$, $R^4$, X and Y are as defined in the specification, and pharmaceutically acceptable salts thereof, in the manufacture of a medicament, for the treatment or prophylaxis of diseases or conditions in which inhibition of the enzyme myeloperoxidase (MPO) is beneficial. Certain novel compounds of formula (Ia) or (Ib) and pharmaceutically acceptable salts thereof are disclosed, together with processes for their preparation. The compounds of formulae (Ia) and (Ib) are MPO inhibitors and are thereby particularly useful in the treatment or prophylaxis of neuroinflammatory disorders.

1 Claim, No Drawings

FOREIGN PATENT DOCUMENTS

| | | |
|---|---|---|
| WO | 9618400 | 6/1996 |
| WO | WO 9618400 A1 * | 6/1996 |
| WO | 9914204 | 3/1999 |
| WO | 9917773 A1 | 4/1999 |
| WO | 9936073 | 7/1999 |
| WO | 9940091 | 8/1999 |
| WO | 0051598 A1 | 9/2000 |
| WO | 0059449 | 10/2000 |
| WO | 01011967 | 2/2001 |
| WO | WO 0111967 A1 * | 2/2001 |
| WO | 0185146 | 11/2001 |
| WO | 0208237 A2 | 1/2002 |
| WO | 02006272 | 1/2002 |
| WO | 02066447 | 8/2002 |
| WO | 02090575 A1 | 11/2002 |
| WO | 03000694 | 1/2003 |
| WO | 03082873 | 10/2003 |
| WO | 2004096781 | 11/2004 |
| WO | 2005037835 A1 | 4/2005 |
| WO | 2005042534 | 5/2005 |
| WO | 2005077950 A2 | 8/2005 |
| WO | 2006045564 A1 | 5/2006 |
| WO | 2006046910 | 5/2006 |
| WO | 2006062465 | 6/2006 |
| WO | 2007142576 | 12/2007 |

OTHER PUBLICATIONS

Copy of final Office Action issued for U.S. Appl. No.10/275,824 on Feb. 8, 2007 (U.S. Appl. No.10/275,824, which is now abandoned, published as U.S. publication No. 2004-0029871, which is cited hereinabove).

Non-final Office Action issued for U.S. Appl. No. 10/275,824 on Jun. 19, 2006 (U.S. Appl. No. 10/275,824, which is now abandoned, published as U. S. publication No. 2004-0029871, which is cited hereinabove).

Advisory Action issued for U.S. Appl. No. 10/275,824 on Mar. 15, 2006 (U.S. Appl. No. 10/275,824, which is now abandoned, published as U.S. publication No. 2004-0029871, which is cited hereinabove).

Final Office Action issued for U.S. Appl. No. 10/275,824 on Nov. 30, 2005 (U.S. Appl. No. 10/275,824, which is now abandoned, published as U.S. publication No. 2004-0029871, which is cited hereinabove).

Non-final Office Action issued for U.S. Appl. No. 10/275, 824 on Jun. 17, 2005 (U.S. Appl. No. 10/275,824, which is now abandoned, published as U.S. publication No. 2004-0029871, which is cited hereinabove).

U.S. Appl. No. 11/756,967, filed Jun. 1, 2007.

Imai et al., "Studies on Nucleic Acid Antagonists. VII. Synthesis and Characterization of 1,4,6-Triazaindenes (5H Pyrrolo(3,2-d)pyrimidines)" Chem. Pharm. Bull., 1964, vol. 12, No. 9, pp. 1030-1042.

Kolasa et al., "Reactions of Alpha-Hydroxy Carbonyl Compounds With Azodicarboxylates and Triphenylphosphine: Synthesis of Alpha-N-Hydroxy Amino Acid Derivatives," Journal of Organic Chemistry, 1987, vol. 52, pp. 4978-4984.

Rao et al., "Synthesis of 5,7-Disubstituted-4-Beta-D-ribofuranosylpyrazolo[4,3-c]-pyrimidines and 2,4-Disubstituted-1-Beta-D-ribofuranosylpyrrolo[3,2-d]-pyrimidines as Congeners of Uridine and Cytidine," J. Heterocyclic Chemistry, 1992, vol. 29, pp. 343-354.

English abstract for WO 2002006272, 2002.

Co-Pending U.S. Appl. No. 11/756,967, filed on Jun. 1, 2007.

Co-Pending U.S. Appl. No. 11/577,833, filed on Apr. 24, 2007.

Co-Pending U.S. Appl. No. 11/720,913, filed on Jun. 5, 2007.

Souness et al., Immunopharmacology 47 (2000) 127-162).

Armitage et al., "Structure-Activity Relationships in a Series of 6-Thioxanthines with Bronchodilator and Coronary Dilator Properties," British Journal of Pharmacology and Chemotherapy (1961), vol. 17, pp. 196-207.

Wooldridge et al., "The Synthesis of Some 6-Thioxanthines," J. Chem. Soc., 1962, pgs. 1863-1868.

Garst et al., "Inhibition of Separated Forms of Phosphodiesterases from Pig Coronary Arteries by Uracils and by 7-Substituted Derivatives of 1-Methyl-3-isobutylxanthine," J. Med. Chem.; 1976; vol. 19(4) pp. 499-503.

Katritzky et al., "A General Method for the N-Alkylation of Thioamides," Tetrahedron Letters, (1988), vol. 29(15), pp. 1755-1758.

Merlos et al., "Structure-Activity Relationships in a Series of Xanthine Derivatives with Antibronchoconstrictory and Bronchodilatory Activities," Eur. J. Med .Chem. Chim. Ther., 1990, vol. 25, ppp. 653-658.

Woo et al., "Inhibitors of Human Purine Nucleoside Phosphorylase. Synthesis and Biological Activities of 8-Amino-3-benzylhypoxanthine and Related Analogues," J. Med. Chem., 1992; vol. 35, pp. 1451-1457.

Van Der Goot et al., "Isothiourea Analogues of Histamine as Potent Agonists or Antagonists of the Histamine H3-Receptor," Eur. J. Med. Chem., 1992, vol. 27, pp. 511-517.

Van Galen et al., "A Binding Site Model and Structure-Activity Relationships for the Rat A3 Adenosine Receptor," Molecular Pharmacology, 1994, vol. 45, pp. 1101-1111.

Jacobson et al., "1,3-Dialkylxanthine Derivatives Having High Potency as Antagonists at Human A2B Adenosine Receptors," Drug Development Research, 1999, vol. 47, pp. 45-53.

Khimicheskaya encyclopedia, ed. By Knunyants I.L., "Sovetskaya encyclopedia", 1990, V. 2, p. 1083.

English translation of Khimicheskaya encyclopedia, p. 1083, 1990.

English abstract for CN1013676, STN International CAPLUS 1986:626214.

International Search Report issued for PCT/SE03/00617, issued on Aug. 5, 2003.

Aaron, S D et al., "Granulocyte Inflammatory Markers and Airway Infection during Acute Exacerbation of Chronic Obstructive Pulmonary Disease," Am J Respir Crit Care Med., 2001, pp. 349-355, vol. 163.

Akbiyik et al., "In vitro and in vivo inhibition of myeloperoxidase with 5-fluorouracil," Eur. J. Clin. Pharmacol., 2001, vol. 57, pp. 631-636.

Baldus, S. et al "Myeloperoxidase Serum Levels Predict Risk in Patients with Acute Coronary Syndromes," Circulation, 2003, pp. 1440-1445, vol. 108.

Berlow et al., "The Effect of Dapsone in Steroid-Dependent Asthma," 1991, J. Allergy Clin. Immunol., 1991, vol. 87 (3), pp. 710-715.

Bozeman et al., "Inhibition of the human leukocyte enzymes myeloperoxidase and eosinophil peroxidase by dapsone," Biochemical Pharmacology, 1992, vol. 44, No. 3, pp. 553-563.

Brennan, M. et al., "Prognostic Value of Myeloperoxidase in Patients with Chest Pain," N. Engl J Med., 2003, pp. 1595-1604, vol. 349, No. 17.

Choi, D-K et al., "Ablation of the Inflammatory Enzyme Myeloperoxidase Mitigates Features of Parkinson's Disease in Mice," J. Neurosci., 2005, pp. 6594-6600, vol. 25, No. 28.

Crooks, S W et al., "Bronchial Inflammation in Acute Bacterial Exacerbations of Chronic Bronchitis: the Role of Leukotriene B4," European Respiratory Journal, 2000, pp. 274-280, vol. 15, No. 2.

Cuzner, M L et al., "Plasminogen Activators and Matrix Metalloproteases, Mediators of Extracellular Proteolysis in Inflammatory Demyelination of the Central Nervous System," Journal of Neuroimmunology, 1999, pp. 1-14, vol. 94, No. 1-2.

Dallegri et al., Possible Modes of Action of Nimesulide in Controlling Neutrophilic Inflammation, ArzneimittelFoschunglDrug Research, 1995, vol. 45(11), No. 10, pp. 1114-1117.

Daugherty, A. et al., "Myeloperoxidase, a Catalyst for Lipoprotein Oxidation, Is Expressed in Human Atherosclerotic Lesions," J Clin Invest., 1994, pp. 437-444, vol. 94, No. 1.

Fiorini, G. et al., "Serum ECP and MPO are Increased During Exacerbations of Chronic Bronchitis with Airway Obstruction," Biomedicine & Pharmacotherapy, 2000, pgs. 274-278, vol. 54.

Green, P. S et al., "Neuronal Expression of Myeloperoxidase is Increased in Alzheimer's Disease," Journal of Neurochemistry, 2004, pp. 724-733, vol. 90, No. 3.

Grisham et al., "Assessment of Leukocye involvement during Ischemia and Reperfusion of Intestine," Am. J. Physiol., 1986, vol. 251, pp. 729-742.

Hampton, M B, et al., "Inside the Neutrophil Phagosome: Oxidants, Myeloperoxidase, and Bacterial Killing," Blood, 1998, pp. 3007-3017, vol. 92, No. 9.

Hope et al., "Large scale purification of myeloperoxidase from HL60 promyelocytic cells: characterization and comparison to human neutrophil myeloperoxidase," Protein Expression and Purification, 2000, vol. 18, pp. 269-276.

Kettle et al., "Assays for the Chlorination Activity of Myeloperoxidase," Biophyl, 1992, vol. 296, pp. 502-512.

Kettle et al., "Mechanism of inhibition of myeloperoxidase by anti-inflammatory drugs," Biochemical Pharmacology, 1991, vol. 41, No. 10, pp. 1485-1492.

Kettle et al., "Superoxide is an Antagonist of Anti-Inflammatory Drugs that Inhibit Hyposchlorous Acid Production by Myeloperoxidase," Biochemical Pharmacology, 1993, vol. 45, No. 10, pp. 2003-2010.

Kutter, D. et al., "Consequences of Total and Subtotal Myeloperoxidase Deficiency: Risk or Benefit'?," Acta Haematol, 2000, pp. 10-15, vol. 104, No. 1.

Leckie et al., "Novel Therapy for COPD," Exp. Opin. Invest. Drugs, 2000, vol. 9(1), pp. 3-23.

Martin et al., "Reduction of Neutrophil-mediated injury to pulmonary endothelial cells by Dapsone 1-3", Am. Rev. Respir Dis., 1985, vol. 131, pp. 544-547.

Nagra, R M, et al., "Immunohistochemical and Genetic Evidence of Myeloperoxidase Involvement in Multiple Sclerosis," Journal of Neuroimmunology, 1997, pp. 97-107, vol. 78, No. 1-2.

Nocker et al., "Interleukin-8 in Airway Inflammation in Patients with Chronic Asthma and Chronic Obstructive Pulmonary Disease," Int. Arch Allergy Immunol., 1996, vol. 109, pp. 183-191.

Ottonello et al., "Sulphonamides as Anti-Inflammatory Agents: Old Drugs for New Therapeutic Strategies in Neutrophilic Inflammation," Clinical Science, 1995, vol. 88, pp. 331-336.

Sugiyama, S. et al., "Macrophage Myeloperoxidase Regulation by Granulocyte Macrophage Colony-Stimulating Factor in Human Atherosclerosis and Implications in Acute Coronary Syndromes," Am J Pathol, 2001, pp. 879-891, vol. 158, No. 3.

Suzuki et al., "Assay method for myeloperoxidase in human polymorphonuclear leukocytes," Analytical Biochemistry, 1983, vol. 132, pp. 345-352.

Van Zyl et al., "Interaction of methylxanthines with myeloperoxidase. An anti-inflammatory mechanism," Intnl J. of Biochem, 1992, vol. 24(6), pp. 929-935.

Zhang, R. et al.,"Association Between Myeloperoxidase Levels and Risk of Coronary Artery Disease," Jama, 2001, pp. 2136-2142, vol. 286, No. 17.

STN Intnl, CAPLUS Accession No. 1968:434597, Doc No. 69:34597, Dietz et al., "The hypnotic properties of 8-ethylthio-6-thiotheophylline sodium" & Toxicology and Applied Pharm., 1968, vol. 12, pp. 202-206.

STN Intnl, CAPLUS Accession No. 1966:420839, Doc No. 65:20839, Dietz et al., "The synthesis and pharmacologic evaluation of a series of 8-alkylthio-thiated theophyylines" & J. of Med Chem., 1966, vol. 9(4), pp. 500-506.

STN Intnl, CAPLUS Accession No. 1966:35888, Doc No. 64:35888, Dietz et al., "Synthesis of some 8-alkylthio-2-thiotheophyllines and 8-alkylthio-6-thiotheophyllines" & J. of Med Chem., 1966, vol. 9(1), p. 160.

STN Intnl CAPLUS Accession No. 1974:82889, No. 80:82889, Reichman, Uri et al., "Tautomerism, ionization and methylation of 2(methylthio)- and 2,8-bis(methyl-thio)hypoxanthines" & J. of the Chem. Soc., Perkin Transactions 1: Organic & BioOrganic Chem, 1972-1999, (22), 2647-55, 1973.

STN Intnl, File CAPLUS Accession No. 1984:630460, Doc No. 101:230460, Talukdar, P.B. et al., "Studies on ring-fused mesoionic thiazolo(3,2-a) imidazolo(4,5-d)pyrimidine derivatives," & Indian J. of Chem, Section B: Organic Chem. Including Medicinal Chem, 23B(4), pp. 316-320, 1984.

STN Intnl, file Registry, 2H-Purin-2-one, 1,3,6,7-tetrahydro-8-(methylthio)-6-thioxo-(9CI) Reg No. 500336-85-6, 2004.

STN Intnl, file Registry, "2-H-Purin-2-one, 1,3,6,7-tetrahydro-8-(propylthio)-6-thioxo-, sodium salt (9CI)" Reg No. 5784-48-5, 2004.

STN Intnl, file Registry, "1H-Purine-2,6-dithione, 3,7-dihydro-1,3-dimethyl-8-(methylthio)-, sodium salt (9CI)" Reg No. 5779-07-7, 2004.

STN Intnl, file Registry, "2h-Purin-2-one, 8-[(1-ethylbutypthio]-1,3,6,7-tetrahydro-1,3-dimethyl-6-thioxo-, sodium salt (9CI)", Reg No. 5779-06-6, 2004.

STN printout for Registry No. 582-33-2: 3-Aminobenzoic acid ethyl ester, 1984.

STN Intnl, Registry No. 2487-40-3, 1982.

English abstract for JP 02160235, Jun. 20, 1990.

\* cited by examiner

THIOXANTHINE DERIVATIVES AS MYELOPEROXIDASE INHIBITORS

CROSS-REFERENCE TO RELATED APPLICATIONS

This application is a continuation of U.S. application Ser. No. 10/511,537, which was the National Stage of International Application No. PCT/SE03/00617, filed Apr. 15, 2003, which claims the benefit under 35 U.S.C. §119 (a)-(d) of Swedish application nos. 0201193-0, filed Apr. 19, 2002, and 0202239-0, filed Jul. 17, 2002, which are all hereby incorporated herein by reference.

FIELD OF THE INVENTION

The present invention relates to the use of thioxanthine derivatives as inhibitors of the enzyme myeloperoxidase (MPO). Certain novel thioxanthine derivatives are also disclosed together with processes for their preparation, compositions containing them and their use in therapy.

BACKGROUND OF THE INVENTION

Myeloperoxidase (MPO) is a heme-containing enzyme found predominantly in polymorphonuclear leukocytes (PMNs). MPO is one member of a diverse protein family of mammalian peroxidases that also includes eosinophil peroxidase, thyroid peroxidase, salivary peroxidase, lactoperoxidase, prostaglandin H synthase, and others. The mature enzyme is a dimer of identical halves. Each half molecule contains a covalently bound heme that exhibits unusual spectral properties responsible for the characteristic green colour of MPO. Cleavage of the disulphide bridge linking the two halves of MPO yields the hemi-enzyme that exhibits spectral and catalytic properties indistinguishable from those of the intact enzyme. The enzyme uses hydrogen peroxide to oxidize chloride to hypochlorous acid. Other halides and pseudohalides (like thiocyanate) are also physiological substrates to MPO.

PMNs are of particular importance for combating infections. These cells contain MPO, with well documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound. Hypochlorous acid is oxidizing in itself, and reacts most avidly with thiols and thioethers, but also converts amines into chloramines, and chlorinates aromatic amino acids. Macrophages are large phagocytic cells which, like PMNs, are capable of phagocytosing microorganisms. Macrophages can generate hydrogen peroxide and upon activation also produce myeloperoxidase. MPO and hydrogen peroxide can also be released to the outside of the cells where the reaction with chloride can induce damage to adjacent tissue.

Linkage of myeloperoxidase activity to disease has been implicated in neurological diseases with a neuroinflammatory response including multiple sclerosis, Alzheimer's disease, Parkinson's disease and stroke as well as other inflammatory diseases or conditions like asthma, chronic obstructive pulmonary disease, cystic fibrosis, atherosclerosis, inflammatory bowel disease, renal glomerular damage and rheumatoid arthritis. Lung cancer has also been suggested to be associated with high MPO levels.

WO 01/85146 discloses various compounds that are MPO inhibitors and are thereby useful in the treatment of chronic obstructive pulmonary disease (COPD). 3-n-Propyl-2-thioxanthine is disclosed in Drug Development Research, 1999, 47, 45-53. 3-Isobutyl-6-thioxanthine is disclosed in J. Chem. Soc., 1962, 1863. 2-Thioxanthine is commercially available.

The present invention relates to a group of thioxanthine derivatives that surprisingly display useful properties as inhibitors of the enzyme MPO.

DISCLOSURE OF THE INVENTION

According to the present invention, there is provided the use of a compound of formula (Ia) or (Ib)

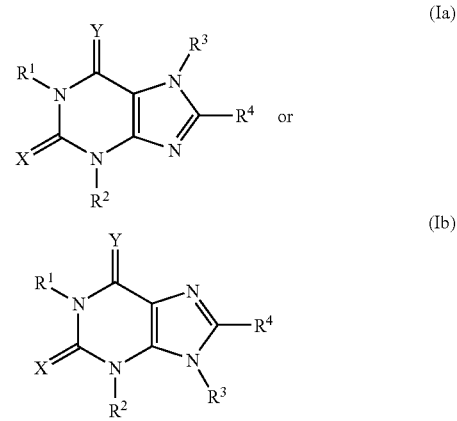

wherein:
one of X and Y represents S, and the other represents O or S;
$R^1$ represents hydrogen or C1 to 6 alkyl;
$R^2$ represents hydrogen or C1 to 6 alkyl; said alkyl group being optionally substituted by:
i) a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy; or
ii) C1 to 6 alkoxy; or
iii) an aromatic ring selected from phenyl, furyl or thienyl; said aromatic ring being optionally further substituted by halogen, C1 to 6 alkyl or C1 to 6 alkoxy;
$R^3$ and $R^4$ independently represent hydrogen or C1 to 6 alkyl;
or a pharmaceutically acceptable salt thereof, in the manufacture of a medicament, for the treatment or prophylaxis of diseases or conditions in which inhibition of the enzyme MPO is beneficial.

The compounds of formula (Ia) or (Ib) may exist in enantiomeric forms. Therefore, all enantiomers, diastereomers, racemates and mixtures thereof are included within the scope of the invention.

It will be appreciated that when $R^3$ in formulae (Ia) and (Ib) represents hydrogen, the two alternative representations (Ia) and (Ib) are tautomeric forms of the same compound. All such tautomers and mixtures of tautomers are included within the scope of the present invention.

A more particular aspect of the invention provides the use of a compound of formula (Ia) or (Ib), or a pharmaceutically acceptable salt thereof, in the manufacture of a medicament, for the treatment or prophylaxis of neuroinflammatory disorders.

According to the invention, there is also provided a method of treating, or reducing the risk of, diseases or conditions in which inhibition of the enzyme MPO is beneficial which comprises administering to a person suffering from or at risk of, said disease or condition, a therapeutically effective amount of a compound of formula (Ia) or (Ib), or a pharmaceutically acceptable salt thereof.

More particularly, there is also provided a method of treating, or reducing the risk of, neuroinflammatory disorders in a person suffering from or at risk of, said disease or condition, wherein the method comprises administering to the person a therapeutically effective amount of a compound of formula (Ia) or (Ib), or a pharmaceutically acceptable salt thereof.

In another aspect the invention provides a pharmaceutical formulation comprising a therapeutically effective amount of a compound of formula (Ia) or (Ib), or a pharmaceutically acceptable salt thereof, in admixture with a pharmaceutically acceptable adjuvant, diluent or carrier, for use in the treatment or prophylaxis of diseases or conditions in which inhibition of the enzyme MPO is beneficial.

In another more particular aspect the invention provides a pharmaceutical formulation comprising a therapeutically effective amount of a compound of formula (Ia) or (Ib), or a pharmaceutically acceptable salt thereof, in admixture with a pharmaceutically acceptable adjuvant, diluent or carrier, for use in the treatment or prophylaxis of neuroinflammatory disorders.

In one embodiment, there is provided the use of a compound of formula (Ia) or (Ib) wherein at least one of X and Y represents S, and the other represents O or S; $R^1$ represents hydrogen or C1 to 6 alkyl; $R^2$ represents hydrogen or C1 to 6 alkyl; said alkyl group being optionally substituted by C3 to 7 cycloalkyl, C1 to 4 alkoxy, or an aromatic ring selected from phenyl, furyl or thienyl; said aromatic ring being optionally further substituted by halogen, C1 to 4 alkyl or C1 to 4 alkoxy; $R^3$ and $R^4$ independently represent hydrogen or C1 to 6 alkyl; or a pharmaceutically acceptable salt, enantiomer or racemate thereof, in the manufacture of a medicament, for the treatment or prophylaxis of diseases or conditions in which inhibition of the enzyme MPO is beneficial.

In another embodiment, there is provided the use of a compound of formula (Ia) or (Ib) wherein at least one of X and Y represents S, and the other represents O or S; $R^1$ represents hydrogen or C1 to 6 alkyl; $R^2$ represents hydrogen or C1 to 6 alkyl; said alkyl group being optionally substituted by: i) a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 4 alkoxy; or ii) C1 to 4 alkoxy; or iii) an aromatic ring selected from phenyl, furyl or thienyl; said aromatic ring being optionally further substituted by halogen, C1 to 4 alkyl or C1 to 4 alkoxy; $R^3$ and $R^4$ independently represent hydrogen or C1 to 6 alkyl; or a pharmaceutically acceptable salt thereof, in the manufacture of a medicament, for the treatment or prophylaxis of diseases or conditions in which inhibition of the enzyme MPO is beneficial.

In one embodiment, the invention relates to the use of compounds of formula (Ia) or (Ib) wherein X represents S and Y represents O.

In another embodiment, $R^3$ in formula (Ia) or (Ib) represents hydrogen.

In another embodiment, $R^2$ in formula (Ia) or (Ib) represents optionally substituted C1 to 6 alkyl.

In another embodiment, $R^2$ in formula (Ia) or (Ib) represents C1 to 6 alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy.

In another embodiment, $R^2$ in formula (Ia) or (Ib) represents methylene, ethylene or trimethylene substituted by cyclopropyl, cyclohexyl, tetrahydrofuranyl or morpholinyl.

In another embodiment, $R^2$ in formula (Ia) or (Ib) represents C1 to 6 alkyl substituted by C1 to 6 alkoxy.

In another embodiment, $R^2$ in formula (Ia) or (Ib) represents ethylene or trimethylene substituted by methoxy or ethoxy.

When X represents S and Y represents O, a further embodiment comprises compounds of formula (Ia) or (Ib) wherein $R^1$ represents hydrogen.

When X represents S and Y represents O, a yet further embodiment comprises compounds of formula (Ia) or (Ib) wherein $R^4$ represents hydrogen.

When X represents O and Y represents S, a further embodiment comprises compounds of formula (Ia) or (Ib) wherein $R^1$ represents C1 to 6 alkyl.

When X represents O and Y represents S, a yet further embodiment comprises compounds of formula (Ia) or (Ib) wherein $R^4$ represents C1 to 6 alkyl.

In one embodiment, the invention relates to the use of compounds of formula (Ia) or (Ib) wherein X represents S and Y represents O; $R^2$ represents optionally substituted C1 to 6 alkyl; and $R^1$, $R^3$ and $R^4$ each represent hydrogen.

In one embodiment, the invention relates to the use of compounds of formula (Ia) or (Ib) wherein X represents S and Y represents O; $R^2$ represents C1 to 6 alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy; and $R^1$, $R^3$ and $R^4$ each represent hydrogen.

In one embodiment, the invention relates to the use of compounds of formula (Ia) or (Ib) wherein X represents S and Y represents O; $R^2$ represents C1 to 6 alkyl substituted by C1 to 6 alkoxy; and $R^1$, $R^3$ and $R^4$ each represent hydrogen.

A specific aspect of the invention concerns the use of the following compounds of formula (Ia) or (Ib):
1,3-diisobutyl-8-methyl-6-thioxanthine;
1,3-dibutyl-8-methyl-6-thioxanthine;
3-isobutyl-1,8-dimethyl-6-thioxanthine;
3-(2-methylbutyl)-6-thioxanthine;
3-isobutyl-8-methyl-6-thioxanthine;
3-isobutyl-2-thioxanthine;
3-isobutyl-2,6-dithioxanthine;
3-isobutyl-8-methyl-2-thioxanthine;
3-isobutyl-7-methyl-2-thioxanthine;
3-cyclohexylmethyl-2-thioxanthine;
3-(3-methoxypropyl)-2-thioxanthine;
3-cyclopropylmethyl-2-thioxanthine;
3-isobutyl-1-methyl-2-thioxanthine;

3-(2-tetrahydrofuryl-methyl)-2-thioxanthine;
3-(2-methoxy-ethyl)-2-thioxanthine;
3-(3-(1-morpholinyl)-propyl)-2-thioxanthine;
3-(2-furyl-methyl)-2-thioxanthine;
3-(4-methoxybenzyl)-2-thioxanthine;
3-(4-fluorobenzyl)-2-thioxanthine;
3-phenethyl-2-thioxanthine;
(+)-3-(2-tetrahydrofuryl-methyl)-2-thioxanthine;
(−)-3-(2-tetrahydrofuryl-methyl)-2-thioxanthine;
3-n-butyl-2-thioxanthine;
3-n-propyl-2-thioxanthine;
3-isobutyl-6-thioxanthine;
2-thioxanthine;
and pharmaceutically acceptable salts thereof.

Unless otherwise indicated, the term "C1 to 6 alkyl" referred to herein denotes a straight or branched chain alkyl group having from 1 to 6 carbon atoms. Examples of such groups include methyl, ethyl, 1-propyl, n-butyl, iso-butyl, tert-butyl, pentyl and hexyl.

The term "C1 to 4 alkyl" is to be interpreted analogously.

Unless otherwise indicated, the term "C3 to 7 cycloalkyl" referred to herein denotes a cyclic alkyl group having from 3 to 7 carbon atoms. Examples of such groups include cyclopropyl, cyclopentyl and cyclohexyl.

Unless otherwise indicated, the term "C1 to 6 alkoxy" referred to herein denotes a straight or branched chain alkoxy group having from 1 to 6 carbon atoms. Examples of such groups include methoxy, ethoxy, 1-propoxy, 2-propoxy and tert-butoxy.

The term "C1 to 4 alkoxy" is to be interpreted analogously.

Unless otherwise indicated, the term "halogen" referred to herein denotes fluoro, chloro, bromo and iodo.

Examples of a saturated or partially unsaturated 3- to 7-membered ring optionally incorporating one or two heteroatoms selected independently from O, N and S, and optionally incorporating a carbonyl group include cyclopropyl, cyclopentyl, cyclohexyl, cyclopentanone, tetrahydrofuran, pyrrolidine, piperidine, morpholine, piperazine, pyrrolidinone and piperidinone. Particular examples include cyclopropyl, cyclohexyl, tetrahydrofuranyl (tetrahydrofuryl) and morpholinyl.

Certain compounds of formula (Ia) or (Ib) are novel. Therefore a further aspect of the invention provides the following novel compounds of formula (Ia) or (Ib)

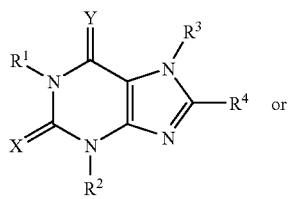

(Ia)

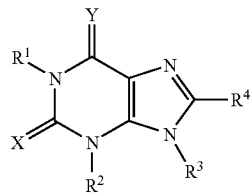

(Ib)

wherein:
X represents S, and Y represents O;
R¹ represents hydrogen or C1 to 6 alkyl;

R² represents C1 to 6 alkyl substituted by a saturated or partially unsaturated 3- to 7-membered ring optionally incorporating one or two heteroatoms selected independently from O, N and S, and optionally incorporating a carbonyl group; said ring being optionally substituted by one or more substituents selected from halogen, hydroxy, C1 to 6 alkoxy and C1 to 6 alkyl; said alkyl being optionally further substituted by hydroxy or C1 to 6 alkoxy;
R³ and R⁴ independently represent hydrogen or C1 to 6 alkyl; and pharmaceutically acceptable salts thereof.

A further aspect of the invention provides the following novel compounds of formula (Ia) or (Ib):
1,3-diisobutyl-8-methyl-6-thioxanthine;
1,3-dibutyl-8-methyl-6-thioxanthine;
3-isobutyl-1,8-dimethyl-6-thioxanthine;
3-(2-methylbutyl)-6-thioxanthine;
3-isobutyl-8-methyl-6-thioxanthine;
3-isobutyl-2-thioxanthine;
3-isobutyl-2,6-dithioxanthine;
3-isobutyl-8-methyl-2-thioxanthine;
3-isobutyl-7-methyl-2-thioxanthine;
3-cyclohexylmethyl-2-thioxanthine;
3-(3-methoxypropyl)-2-thioxanthine;
3-cyclopropylmethyl-2-thioxanthine;
3-isobutyl-1-methyl-2-thioxanthine;
3-(2-tetrahydrofuryl-methyl)-2-thioxanthine;
3-(2-methoxy-ethyl)-2-thioxanthine;
3-(3-(1-morpholinyl)-propyl)-2-thioxanthine;
3-(2-furyl-methyl)-2-thioxanthine;
3-(4-methoxybenzyl)-2-thioxanthine;
3-(4-fluorobenzyl)-2-thioxanthine;
3-phenethyl-2-thioxanthine;
(+)-3-(2-tetrahydrofuryl-methyl)-2-thioxanthine;
(−)-3-(2-tetrahydrofuryl-methyl)-2-thioxanthine;
3-n-butyl-2-thioxanthine;
and pharmaceutically acceptable salts thereof.

A further aspect of the invention is the use of the novel compounds of formula (Ia) or (Ib) as a medicament.

According to the invention, we further provide a process for the preparation of the novel compounds of formula (Ia) or (Ib), or a pharmaceutically acceptable salt, enantiomer, diastereomer or racemate thereof which comprises:
(a) reaction of a compound of formula (IIa) or (IIb)

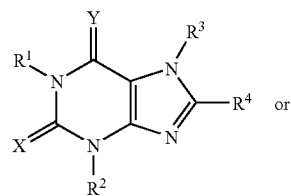

(IIa)

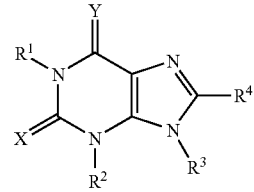

(IIb)

wherein R¹, R², R³ and R⁴ are as defined in formula (Ia) or (Ib), X represents O or S and Y represents O;
with a sulphurising compound such as Lawesson's reagent or phosphorus pentasulphide; to give a corresponding compound wherein Y represents S; or (b) reaction of a diamine of formula (IIIa) or (IIIb)

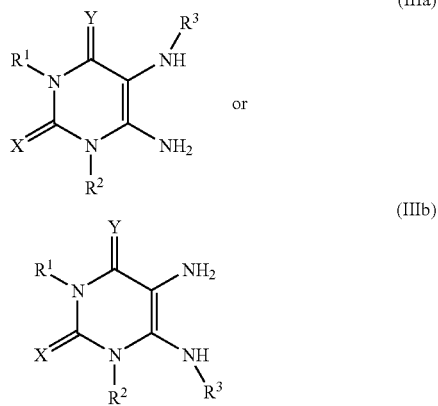

wherein $R^1$, $R^2$, $R^3$, X and Y are as defined in formula (Ia) or (Ib);
with formic acid or with a trialkylorthoester;
and where necessary converting the resultant compound of formula (Ia) or (Ib), or another salt thereof, into a pharmaceutically acceptable salt thereof, or converting the resultant compound of formula (Ia) or (Ib) into a further compound of formula (Ia) or (Ib); and where desired converting the resultant compound of formula (Ia) or (Ib) into an optical isomer thereof.

In process (a), a compound of formula (Ia) or (IIb) and a sulfurising agent such as Lawesson's reagent, or phosphorus pentasulfide are dissolved or suspended in a suitable dry organic solvent such as benzene, toluene, xylene, tetrahydrofuran, dichloromethane or dioxane and then heated to between 30° C. and the reflux temperature of the solvent until reaction is complete, typically for between one to 30 hours. The reaction mixture is then cooled and filtered to remove insoluble solids. The solvent is removed under reduced pressure and the crude product is purified by column chromatography or by recrystallisation.

In process (b), a diamine of formula (IIIa) or (IIIb) is treated at a suitable temperature with an excess of an appropriate ortho ester such as triethylorthoformate, triethylorthoacetate, triethylorthopropionate, triethylorthobutanoate, tripropylorthoformate, tributylorthoformate and triisopropylorthoformate, optionally in the presence of a suitable solvent such as an alcohol, until reaction is complete. The temperature is typically up to the reflux temperature of the reaction mixture, and reaction times are generally from 30 minutes to overnight. In one embodiment, the orthoester is triethylorthoformate with ethanol as an optional solvent.

Alternatively in process (b), a diamine of formula (IIIa) or (IIIb) is treated with 98% formic acid at a suitable temperature between ambient temperature and the reflux temperature of the reaction mixture. The process is continued for a suitable period of time, typically for between 0.5 to 5 hours. After removal of the formic acid, treatment with a suitable aqueous base, for example, with 10% aqueous sodium hydroxide solution, then yields the compound of formula (I). The treatment with base is carried out for a suitable time at a suitable temperature, for example, for about 10 minutes to 4 hours at a temperature between ambient temperature and the reflux temperature of the reaction mixture.

Other methods for the conversion of a diamine of formula (IIIa) or (IIIb) into a compound of formula (Ia) or (Ib) are described in the literature and will be readily known to the person skilled in the art.

The present invention includes compounds of formula (Ia) or (Ib) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (Ia) or (Ib) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxan, ethanol, tetrahydrofuran or diethyl ether, or a mixture of solvents, which may be removed in vacuo or by freeze drying. The reaction may also be a metathetical process or it may be carried out on an ion exchange resin.

Compounds of formulae (IIa) or (IIb) and compounds of formula (IIIa) or (IIIb) are either known in the literature or may be prepared using known methods that will be readily apparent to the man skilled in the art.

The compounds of the invention and intermediates thereto may be isolated from their reaction mixtures and, if necessary further purified, by using standard techniques.

The compounds of formula (Ia) or (Ib) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively, the various optical isomers may be prepared directly using optically active starting materials.

Intermediate compounds may also exist in enantiomeric forms and may be used as purified enantiomers, diastereomers, racemates or mixtures.

The compounds of formula (Ia) or (Ib), and their pharmaceutically acceptable salts are useful because they possess pharmacological activity as inhibitors of the enzyme MPO.

The compounds of formulae (Ia) and (Ib) and their pharmaceutically acceptable salts are indicated for use in the treatment or prophylaxis of diseases or conditions in which modulation of the activity of the enzyme myeloperoxidase (MPO) is desirable. In particular, linkage of MPO activity to disease has been implicated in neuroinflammatory diseases. Therefore the compounds of the present invention are particularly indicated for use in the treatment of neuroinflammatory conditions or disorders in mammals including man. Such conditions or disorders will be readily apparent to the man skilled in the art.

Conditions or disorders that may be specifically mentioned include multiple sclerosis, Alzheimer's disease, Parkinson's disease, amyotrophic lateral sclerosis and stroke, as well as other inflammatory diseases or conditions such as asthma, chronic obstructive pulmonary disease, cystic fibrosis, idiopathic pulmonary fibrosis, acute respiratory distress syndrome, sinusitis, rhinitis, psoriasis, dermatitis, uveitis, gingivitis, atherosclerosis, inflammatory bowel disease, renal glomerular damage, liver fibrosis, sepsis, proctitis, rheumatoid arthritis, and inflammation associated with reperfusion injury, spinal cord injury and tissue damage/scarring/adhesion/rejection. Lung cancer has also been suggested to be associated with high MPO levels. The compounds are also expected to be useful in the treatment of pain.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formulae (Ia) or (Ib), and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another aspect of the invention concerns a pharmaceutical composition comprising a novel compound of formula (Ia) or (Ib), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formulae (Ia) or (Ib), or a pharmaceutically acceptable salt thereof.

There is also provided a process for the preparation of such a pharmaceutical composition which comprises mixing the ingredients.

The invention is illustrated, but in no way limited, by the following examples:

$^1$H and $^{13}$C NMR spectra were recorded either on a 300 MHz Bruker DPX instrument or on a Varian Unity 400 MHz spectrometer at 25° C. The following reference signals were used: the middle line of DMSO-$d_6$ δ 39.5 ($^{13}$C); DMSO-$d_6$ δ 2.50 ($^1$H). All mass spectra were recorded on a Waters LCMS (2790) instrument. Thin layer chromatography (TLC) was performed on Merck TLC aluminium sheets silica gel 60 $F_{254}$ pre-coated sheets (layer thickness 0.2 mm). Merck Silica gel 60 (0.063-0.200 mm) was used for column chromatography. HPLC analysis were performed on a Gynkotek P580 HPG, gradient pump with a Gynkotek UVD 170S UV-vis detector. Column; Waters symmetry C18, 5 μm, 3.9×150 mm. Preparative liquid chromatography was performed on a Gynkotek P580 HPG, gradient pump with a Gynkotek UVD 170S UV-vis detector. Column; Waters symmetry C18, 5 μm, 19×100 mm.

Starting materials were prepared according to the following references:

1. Merlos, M.; Gomez, L.; Vericat, M. L.; Bartroli, J.; Garcia-Rafanell, J.; Form, J.; *Eur. J. Med. Chem. Chim. Ther.;* 25; 8; 1990; 653-658.
2. Kjellin, P. G.; Persson, C. G. A., EP 0 010 531.
3. Katritzky, A. R.; Drewniak, M., *Tet. Lett.* (1988), 29(15), 1755-1758.
4. Van der Goot, H.; Schepers, M. J. P.; Sterk, G. J.; Timmerman, H., *Eur. J. Med. Chem.* (1992), 27 (5), 511-517.

EXAMPLE 1

13-Diisobutyl-8-methyl-6-thioxanthine 1,3-Diisobutyl-8-methyl-xanthine[1] (0.20 g, 0.72 mmol) and Lawesson's reagent (1.5 g, 3.6 mmol) were suspended in toluene (8 mL) and then heated at 100° C. for 21 h. The reaction mixture was cooled and filtered to remove insoluble solids. The solvent was removed under reduced pressure and the crude product was purified by column chromatography using silica gel and eluting with ethyl acetate/heptane (1:1) giving the title compound (90 mg, 43% yield).

$^1$H NMR (DMSO-$d_6$): δ 13.1 (s, 1H), 4.28 (d, 2H, J 7.2 Hz), 3.84 (d, 2H, J 7.5 Hz), 2.40 (s, 3H), 2.28-2.35 (m, 1H), 2.17-2.25 (m, 1H), 0.85-0.88 (m, 12H).

MS (ES) $^m$/z 295 (M+1).

EXAMPLE 2

1,3-Dibutyl-8-methyl-6-thioxanthine 1,3-Dibutyl-8-methyl-xanthine[1] (0.20 g, 0.72 mmol) and Lawesson's reagent (0.87 g, 2.2 mmol) were suspended in toluene (8 mL) and heated at 120° C. for 30 h. The resulting brown mixture was cooled and the solvent evaporated under reduced pressure. The brownish solid residue was suspended in 10% sodium hydroxide (25 mL) and stirred overnight. Then the pH of the solution was adjusted to pH 4 with 10% acetic acid. The precipitate was collected by filtration and washed with water. This crude product was purified by column chromatography using silica gel and elution with ethyl acetate/heptane (9:1) giving the title compound (0.15 g, 69% yield).

$^1$H NMR (DMSO-$d_6$): δ 13.1 (s, 1H), 4.40 (t, 2H, J 7.6 Hz), 3.99 (t, 2H, J 7.3 Hz), 2.40 (s, 3H), 1.57-1.69 (m, 4H), 1.28-1.35 (m, 4H), 0.88-0.93 (m, 6H).

$^{13}$C NMR (DMSO-$d_6$): δ 173.5, 154.2, 148.9, 143.2, 118.9, 45.61, 43.13, 29.24, 28.37, 19.51, 19.31, 14.42, 13.60.

MS (ES) $^m$/z 295 (M+1).

EXAMPLE 3

3-Isobutyl-1,8-dimethyl-6-thioxanthine 1,3-Isobutyl-1,8-dimethyl-xanthine[1] (0.150 g, 6.35 mmol, 1.0 eq.) and Lawesson's reagent (0.128 g, 3.17 mmol, 0.5 eq.) were dissolved in toluene (10 mL) and the reaction mixture was heated to reflux for 3.5 h. The conversion was less than 10% according to HPLC. Lawesson's reagent (0.5 g) was added and the reaction mixture was heated to reflux overnight. The solvent was evaporated off and the remaining brown solid was purified by preparative HPLC to give the title compound (78 mg, 49%).

$^1$H NMR (DMSO-$d_6$): δ 13.16 (s, 1H), 3.92 (d, 2H), 3.77 (s, 3H), 2.50 (s, 3H), 2.35 (m, 1H), 0.97 (d, 6H).

EXAMPLE 4

3-(2-Methylbutyl)-6-thioxanthine 3-(2-Methylbutyl)-xanthine[2] (3 g, 0.013 mol) and phosphorus pentasulfide (5 g, 0.025 mol) in dioxane (250 mL) were refluxed for 3 h. Almost 150 mL dioxane was distilled off and the solution was cooled down. Water (100 mL) was added and the mixture was stirred at room temperature for 2 h. 2N Sodium hydroxide (75 mL) was added, the solution was filtered and neutralized with 5N hydrochloric acid. The crude crystals were filtered off and recrystallised from ethanol to yield the title compound (1.6 g, 51%).

$^1$H NMR (DMSO-d$_6$): δ 13.53 (s, 1H), 12.32 (s, 1H), 8.11 (s, 1H), 3.85 (dd, 1H, $^2$J 13.1 Hz, $^3$J 7.1 Hz), 3.78 (dd, 1H, $^2$J 13.1 Hz, $^3$J 8.1 Hz), 2.00 (m, 1H), 1.36 (m, 1H), 1.14 (m, 1H), 0.87 (t, 3H, J 7.6), 0.82 (d, 3H, J 6.6).

$^{13}$C NMR (DMSO-d$_6$): δ 175.11, 149.19, 145.73, 143.62, 118.32, 48.11, 32.93, 26.40, 16.57, 11.05.

EXAMPLE 5

3-Isobutyl-8-methyl-6-thioxanthine

3-Isobutyl-8-methyl-xanthine[2] (4.5 g, 0.02 mol) and phosphorus pentasulfide (8 g, 0.04 mol) in dioxane (400 mL) were refluxed for 5 h. Almost 200 mL dioxane was distilled off and the solution was cooled down. Water (250 mL) was added and the mixture was stirred at room temperature for 2 h. 2N Sodium hydroxide (150 mL) was added, the solution was filtered and neutralized with 5N hydrochloric acid, and the solution was left overnight. The crude crystals were filtered off and washed with water, giving the required product (4.3 g). A portion (2.3 g) was recrystallised from acetic acid to give pure product (1.5 g, 31% overall).

$^1$H NMR (DMSO-d$_6$): δ 13.13 (s, 1H), 12.16 (s, 1H), 3.77 (d, 2H, J 8.1 Hz), 2.38 (s, 3H), 2.20 (m, 1H), 0.86 (d, 3H, J 7.1).

$^{13}$C NMR (DMSO-d$_6$): δ 173.19, 154.23, 149.14, 146.11, 118.56, 49.29, 26.63, 19.73, 14.54.

EXAMPLE 6

3-Isobutyl-2-thioxanthine a) 6-Amino-1-isobutyl-2-thioxo-2,3-dihydro-1H-pyrimidin-4-one Isobutylthiourea[3] (3.8 g, 29 mmol) and ethyl cyanoacetate (3.9 g, 34 mmol) were added to a solution of sodium ethoxide [made from sodium (0.72 g, 32 mmol) and absolute ethanol (30 mL)]. The resulting mixture was refluxed for 4 h. After cooling to room temperature, the solvent was evaporated under reduced pressure. 10% Acetic acid (45 mL) was added to the viscous syrup. The resulting precipitate was collected by filtration and the solid was washed with water. Recrystallisation from methanol/water gave the desired product (4.0 g, 70%).

$^1$H NMR (DMSO-d$_6$): δ 11.8 (s, 1H), 6.99 (s, 2H), 4.85 (m, 2H), 4.61 (broad s, 1H), 2.29 (m, 1H), 0.87 (d, 6H, J 6.6 Hz).

MS (ES) $^m$/z 200 (M+1).

b) 6-Amino-1-isobutyl-5-nitroso-2-thioxo-2,3-dihydro-1H-pyrimidin-4-one

6-Amino-1-isobutyl-2-thioxo-2,3-dihydro-1H-pyrimidin-4-one (1.0 g, 5.0 mmol) was suspended in 10% acetic acid (20 mL). Sodium nitrite (0.38 g, 5.5 mmol) was added and the resulting mixture was heated at 75° C. for 1 h. The reaction mixture became first pink and then purple. The purple mixture was cooled to room temperature. Then water (20 mL) was added and the purple solid was collected by filtration and washed with water to give the title compound (1.1 g, 92% yield). This solid was used in the following step without further purification.

$^1$H NMR (DMSO-d$_6$): δ 13.1 (broad s, 1H), 12.8 (broad s, 1H), 9.1 (broad s, 1H), 4.80 (broad s, 1H), 3.78 (broad s, 1H), 2.21 (m, 1H), 0.88 (d, 6H, J 6.3 Hz).

MS (ES) $^m$/z 229 (M+1).

c) δ 6-Diamino-1-isobutyl-2-thioxo-2,3-dihydro-1H-pyrimidin-4-one

6-Amino-1-isobutyl-5-nitroso-2-thioxo-2,3-dihydro-1H-pyrimidin-4-one (1.1 g, 4.5 mmol) was suspended in 32% aqueous ammonia (10 mL) and water (10 mL) was added. This red mixture was heated at 75° C. Sodium dithionite was added in small portions. When 1.8 g (10 mmol) of dithionite had been added the colour of the solution had changed from red to pale yellow. At this point, all solid was dissolved. After heating for another 5 minutes a precipitate was formed in the solution. The reaction mixture was removed from the oil bath and stirred at ambient temperature for 45 minutes. The pH of the solution was adjusted to neutral pH with 10% acetic acid. The yellow precipitate was collected by filtration and washed with water and dried to yield the diamine (0.76 g, 77%). This product was used without further purification.

$^1$H NMR (DMSO-d$_6$): δ 11.3 (broad s, 1H), 6.19 (s, 2H), 4.94 (broad s, 1H), 3.70 (broad s, 1H), 3.43 (s, 2H), 2.27-2.35 (m, 1H), 0.88 (d, 6H, J 6.1 Hz).

MS (ES) $^m$/z 215 (M+1).

d) 3-Isobutyl-2-thioxanthine 5,6-Diamino-1-isobutyl-2-thioxo-2,3-dihydro-1H-pyrimidin-4-one (0.22 g, 1.0 mmol) was suspended in formic acid (1.5 mL) and this solution was heated at 100° C. for 1 h. Excess formic acid was evaporated off under reduced pressure. 10% Sodium hydroxide (1.5 mL) was added to the orange solid and the resulting solution was heated at 100° C. for 15 minutes. Water was added and the pH of the solution adjusted to pH 4 with dilute acetic acid. The resulting slurry was stirred for 0.5 h at ambient temperature, then the precipitate was collected by filtration and washed with water. Yield: (0.21 g, 90%).

$^1$H NMR (DMSO-d$_6$): δ 13.82 (s, 1H), 12.42 (s, 1H), 8.15 (s, 1H), 4.31 (d, 2H, J 7.6 Hz), 2.50 (m, 1H), 0.88 (d, 6H, J 6.6 Hz).

$^{13}$C NMR (DMSO-d$_6$): δ 173.81, 152.57, 149.79, 141.19, 110.68, 54.04, 26.11, 19.79.

MS (ES) $^m$/z 225 (M+1).

EXAMPLE 7

3-Isobutyl-2,6-dithioxanthine

3-Isobutyl-2-thioxanthine (0.20 g, 0.89 mmol) and Lawesson's reagent (1.1 g, 2.7 mmol) were suspended in toluene (8 mL). This mixture was heated at 120° C. for 17 h. The reaction mixture was cooled and the solvent removed under reduced pressure. 10% Sodium hydroxide (20 mL) was added and the mixture stirred for 10 minutes. This solution was filtered to remove insoluble solids and the solid washed with 10% sodium hydroxide solution. The basic filtrate was treated with dilute acetic acid until pH 4 was reached. The resulting precipitate was collected by filtration and washed with water. Drying of the substance afforded the title compound (0.16 g, 73%).

$^1$H NMR (DMSO-d$_6$): δ 13.9 (s broad, 1H), 13.5 (s broad, 1H), 8.27 (s, 1H), 4.32 (d, 2H, J 7.5 Hz), 2.48-2.55 (m, 1H), 0.89 (d, 6H, J 6.7 Hz).

13C NMR (DMSO-$d_6$): δ 173.3, 172.0, 144.9, 144.5, 122.8, 54.9, 26.3, 20.2.
MS (ES) $^m$/z 241 (M+1).

EXAMPLE 8

3-Isobutyl-8-methyl-2-thioxanthine

A mixture of 5,6-diamino-1-isobutyl-2-thioxo-2,3-dihydro-1H-pyrimidin-4-one (Example 6 (c), 0.70 g, 3.26 mmol) and triethylorthoacetate (10 mL) was heated at 130° C. for 2 h and 40 minutes. Then the reaction mixture was cooled on an ice-bath, the solid filtered off and washed with ethanol (4×2 mL). The solid was dried in vacuo yielding the title compound (0.71 g, 95%).

1H NMR (DMSO-$d_6$): δ 13.45 (s, 1H), 12.33 (s, 1H), 4.28 (d, 2H, J 7.6 Hz), 2.50 (m, 1H), 2.39 (s, 3H), 0.87 (d, 6H, J 6.6 Hz).
13C NMR (DMSO-$d_6$): δ 173.47, 152.09, 151.18, 150.01, 110.62, 53.96, 26.08, 19.75, 14.41.
MS (ES) $^m$/z 239 (M+1).

EXAMPLE 9

3-Isobutyl-7-methyl-2-thioxanthine a) N-(6-Amino-1-isobutyl-4-oxo-2-thioxo-1,2,3,4-tetrahydro-pyrimidin-5-yl)-formamide 5,6-Diamino-1-isobutyl-2-thioxo-2,3-dihydro-1H-pyrimidin-4-one (Example 6 (c), 0.25 g, 1.2 mmol) was dissolved in formic acid (1.5 mL) and stirred at ambient temperature for 0.5 h. A pink precipitate started to form after a few minutes. Water was added and the resulting mixture stirred for 10 minutes. The pink solid was collected by filtration, washed with water and dried to yield the title compound (0.25 g, 86%). This material was used without further purification. NMR showed that the product was obtained as a mixture of two tautomers: formamide (major) and imino (minor).

1H NMR (DMSO-$d_6$): δ 12.0 (broad s, 1H), 8.73 (s, 1H), 8.07 (s, 1H), 6.85 (s, 2H), 4.94 (broad s, 1H), 3.71 (broad s, 1H), 2.22-2.32 (m, 1H), 0.88 (d, 6H, J 6.5 Hz). Additional peaks arising from the imino isomer: 8.12 (d, 1H, J 11.5 Hz), 7.77 (d, 1H, J 11.5 Hz), 7.13 (s, 2H).
MS (ES) $^m$/z 243 (M+1).

b) 6-Amino-1-isobutyl-5-methylamino-2-thioxo-2,3-dihydro-1H-pyrimidin-4-one N-(6-Amino-1-isobutyl-4-oxo-2-thioxo-1,2,3,4-tetrahydro-pyrimidin-5-yl)-formamide (0.25 g, 1.0 mmol) was suspended in dry tetrahydrofuran (5 mL) and borane.dimethylsulphide complex (1M in dichloromethane, 2.5 mL, 2.5 mmol) was added dropwise. The reaction mixture was stirred at ambient temperature for 2.5 h. To the resulting clear yellow solution was added a few drops of 2M hydrochloric acid to eliminate unreacted borane. Water was added and the resulting aqueous solution was extracted with dichloromethane (3×15 mL). The combined organic phase was washed with brine and dried over $Na_2SO_4$. The solvent was evaporated off under reduced pressure yielding the title compound (0.12 g, 54% yield). This material was used without further purification.

1H NMR (DMSO-$d_6$): δ 11.9 (broad s, 1H), 5.75 (s, 2H), 4.94 (broad s, 1H), 3.70 (broad s, 1H), 3.43 (s, 2H), 2.38 (s, 3H), 2.24-2.32 (m, 1H), 0.87 (d, 6H, J 6.8 Hz).
MS (ES) $^m$/z 229 (M+1).

c) 3-Isobutyl-7-methyl-2-thioxanthine

6-Amino-1-isobutyl-5-methylamino-2-thioxo-2,3-dihydro-1H-pyrimidin-4-one (0.11 g, 0.48 mmol) was dissolved in formic acid (1 mL) and heated at 85° C. for 1 h. The excess of formic acid was evaporated off under reduced pressure. 10% Sodium hydroxide solution (2 mL) was added and the solution was heated at 85° C. for 20 minutes. Water was added and the pH was adjusted to 4 with dilute acetic acid, upon which a white solid precipitated. The white solid was collected by filtration, washed with water and dried to yield the title compound (85 mg, 74%).

1H NMR (DMSO-$d_6$): δ 12.4 (s, 1H), 8.10 (s, 1H), 4.28 (d, 2H, J 7.5 Hz), 3.89 (s, 3H), 2.44-2.50 (m, 1H), 0.88 (d, 6H, J 6.7 Hz).
13C NMR (DMSO-$d_6$): δ 174.3, 153.2, 150.1, 143.7, 111.2, 54.1, 33.6, 26.4, 20.1.
MS (ES) $^m$/z 239 (M+1).

EXAMPLE 10

3-Cyclohexylmethyl-2-thioxanthine a) 6-Amino-1-cyclohexylmethyl-2-thioxo-2,3-dihydro-1H-pyrimidin-4-one

The title compound was prepared in accordance with the general method of Example 6 (a) using cyclohexylmethylthiourea[4] (3.92 g, 22.7 mmol), yielding the title compound as a white solid (4.87 g, 90%).

1H NMR (DMSO-$d_6$): δ 11.75 (s, 1H), 6.93 (s, 2H), 5.1-4.7 (br m, 1H), 4.83 (s, 1H), 3.55 (broad, 1H), 1.93 (br, 1H), 1.75-1.30 (br m, 5H), 1.10 (br, 5H).

b) 6-Amino-1-cyclohexymethyl-5-nitroso-2-thioxo-2,3-dihydro-1H-pyrimidin-4-one The title compound was prepared in accordance with the general method in Example 6 (b) from 6-amino-1-cyclohexylmethyl-2-thioxo-2,3-dihydro-1H-pyrimidin-4-one (3.75 g, 15.7 mmol), yielding 3.60 g (85%) of the product as a purple solid.

1H NMR: δ 13.5 (br s, 1H), 12.7 (br s, 1H), 9.1 (br s, 1H), 4.84 (br s, 1H), 3.82 (br s, 1H), 1.80 (br, 1H), 1.64-1.59 (br m, 5H), 1.07 (br, 5H).

c) δ 6-Diamino-1-cyclohexylmethyl-2-thioxo-2,3-dihydro-1H-pyrimidin-4-one

The title compound was prepared in accordance with the general method in Example 6 (c) from 6-amino-1-cyclohexylmethyl-5-nitroso-2-thioxo-2,3-dihydro-1H-pyrimidin-4-one (3.60 g, 13.4 mmol) and was used without purification in the next step.

1H NMR (DMSO-$d_6$): δ 6.17 (s, 2H), 5.01 (br, 1H), 4.0-3.0 (very broad, 3H), 1.97 (br, 1H), 1.8-1.3 (br m, 5H), 1.09 (br m, 5H).

d) 3-Cyclohexylmethyl-2-thioxanthine 5,6-Diamino-1-cyclohexylmethyl-2-thioxo-2,3-dihydro-1H-pyrimidin-4-one, (1.44 g, 5.67 mmol) together with triethyl orthoformate (15 mL) was heated at 146° C. for 2 h and 10 minutes. The mixture was allowed to cool to ambient temperature and then further cooled on an ice-bath, followed by addition of heptane (5 mL). After filtration of the suspension and washing with heptane (20 mL), the obtained solid was dried in vacuo. Suspending the solid (1.2 g) in a hot mixture of 2-propanol (125 mL), water (5 mL) and tert-butyl methyl ether (25 mL) gave, after cooling and filtration, a white precipitate which was washed with further tert-butyl methyl ether (5 mL). The solid was dried in vacuo to give the title compound (0.95 g, 63%).

$^1$H NMR (DMSO-$d_6$): δ 13.69 (s, 1H), 12.35 (s, 1H), 8.12 (s, 1H), 4.33 (d, 2H, J 7.1 Hz), 2.18 (m, 1H), 1.49-1.50 (m, 5H), 1.02-1.17 (m, 5H).

$^{13}$C NMR (DMSO-$d_6$): δ 173.65, 152.68, 149.90, 141.41, 110.96, 52.97, 35.31, 30.09, 25.88, 25.32.

MS (ES) $^m$/z 265 (M+1).

EXAMPLE 11

3-(3-Methoxypropyl)-2-thioxanthine a) 6-Amino-1-(3-methoxypropyl)-2-thioxo-2,3-dihydro-1H-pyrimidin-4-one Sodium methoxide (0.81 g, 21.2 mmol, 1.05 eq.) was added to a solution of 3-methoxypropylthiourea (3.00 g, 20.2 mmol) in ethanol (10 mL). Ethyl cyanoacetate (2.18 mL, 20.2 mmol) in ethanol (10 mL) was added and the resulting white slurry was heated to reflux for 2.5 h. The solvent was evaporated and the remaining pale brown oil was treated with 2M acetic acid (15 mL). The white crystals were filtered off and washed with acetic acid to give the title compound (2.10 g, 48%).

$^1$H NMR (DMSO-$d_6$): δ 1.77 (s, 1H), 6.95 (s, 2H), 4.86 (s, 1H), 3.39 (t, 2H), 3.24 (s, 3H), 1.88 (m, 2H).

b) 3-(3-Methoxypropyl)-2-thioxanthine

Acetic acid (25 mL) was added to 6-amino-1-(3-methoxypropyl)-2-thioxo-2,3-dihydro-1H-pyrimidin-4-one (2.00 g, 9.29 mmol) and the red reaction mixture was heated to 90° C. Sodium nitrite (0.71 g, 10.2 mmol) in water (7 mL) was added, the oil bath was removed and the reaction mixture was stirred for 20 minutes. The solvents were co-evaporated with ethanol and the remaining red solid (1.8 g, 79%) was used in the next step without further purification.

Platinum on carbon (0.5 g) was added to a solution of the crude 6-amino-1-(3-methoxypropyl)-5-nitroso 2-thioxo-2,3-dihydro-1H-pyrimidin-4-one (1.80 g, 7.38 mmol) in tetrahydrofuran (80 mL) and water (20 mL) and the reaction mixture was hydrogenated at atmospheric pressure for 2 h. The catalyst was filtered off and the pale brown filtrate was co-evaporated with ethanol (250 mL). The resulting brown solid, 1.6 g, was used in the next step without further purification.

5,6-Diamino-1-cyclohexylmethyl-2-thioxo-2,3-dihydro-1H-pyrimidin-4-one (1.6 g, 12.2 mmol) was dissolved in ethanol (10 mL) and triethyl orthoformate (10 mL) and the reaction mixture was refluxed for 2.5 h. The solvents were evaporated off and the resulting brown solid was purified by flash chromatography (heptane/ethyl acetate, 4:1-1:1) to give the title compound (110 mg, 9%).

$^1$H NMR (DMSO-$d_6$): δ 13.78 (s, 1H), 12.40 (s, 1H), 8.16 (s, 1H), 4.52 (t, 2H, J 7.1 Hz), 3.41 (t, 2H, J 7.1 Hz), 3.21 (s, 3H), 1.98 (m, 2H).

$^{13}$C NMR (DMSO-$d_6$): δ 173.27, 152.63, 149.30, 141.50, 110.94, 69.51, 57.82, 45.47, 26.68.

EXAMPLE 12

3-Cyclopropylmethyl-2-thioxanthine a) 6-Amino-1-cyclopropylmethyl-2-thioxo-2,3-dihydro-1H-pyrimidin-4-one To 1-cyclopropylmethyl-2-thiourea (0.60 g, 4.6 mmol) in ethanol (10 mL) was added sodium methoxide (0.26 g, 4.8 mmol) and, after 5 minutes, ethyl cyanoacetate (0.50 mL, 4.6 mmol). The resulting mixture was heated to reflux for 2 h and 40 minutes followed by evaporation of the solvent under reduced pressure and treatment of the resulting yellow solid with 2M aqueous acetic acid (10 mL) giving a white solid. The solid was collected by filtration and washed with 2M aqueous acetic acid (10 mL), stirred with ethanol (10 mL) followed by evaporation and drying under reduced pressure, giving the title compound (0.51 g, 56%).

MS (ES) $^m$/z 198 (M+1).

b) 3-Cyclopropylmethyl-2-thioxanthine

6-Amino-1-cyclopropylmethyl-2-thioxo-2,3-dihydro-1H-pyrimidin-4-one (0.50 g, 2.5 mmol) was suspended in acetic acid (8 mL) and, after heating at 90° C. for 15 minutes, sodium nitrite (0.19 g, 2.8 mmol) in water (1 mL) was added to the solution. After 15 minutes the heating was removed and the reaction mixture stirred at ambient temperature for 3 h. Ethanol (30 mL) was added and the solvents were removed under reduced pressure. The resulting oil was treated with ethanol (30 mL) and this afforded, upon evaporation and drying, 6-amino-1-cyclopropylmethyl-5-nitroso-2-thioxo-2, 3-dihydro-1H-pyrimidin-4-one (0.61 g) as a red-brown solid.

The crude product (0.61 g) from the previous reaction was dissolved in water (10 mL) and tetrahydrofuran (30 mL) and platinum on carbon (0.30 g) were added. The mixture was subjected to hydrogenation at atmospheric pressure for 4 h, the catalyst was removed by filtration and the solvents were removed under reduced pressure. Evaporation of added ethanol (50 mL) afforded an orange solid. The residue was dissolved in ethanol (10 mL) and triethyl orthoformate (5 mL) was added and the resulting mixture was heated at reflux overnight. Evaporation of the solvent and purification using preparative HPLC afforded the desired compound (38 mg, 6.2% yield from 6-amino-1-cyclopropylmethyl-2-thioxo-2, 3-dihydro-1H-pyrimidin-4-one).

$^1$H NMR (DMSO-$d_6$): δ 13.78 (s, 1H), 12.43 (s, 1H), 8.15 (s, 1H), 4.37 (d, 2H, J 7.1 Hz), 1.50 (m, 1H), 0.52 (m, 2H), 0.45 (m, 2H).

$^{13}$C NMR (DMSO-$d_6$): δ 173.52, 152.62, 149.52, 141.48, 111.02, 51.71, 9.27, 3.50.

MS (ES) $^m$/z 223 (M+1).

EXAMPLE 13

3-Isobutyl-1-methyl-2-thioxanthine a) 1-isobutyl-3-methylthiourea

Methylamine (2M in methanol, 20.0 mL, 40.2 mmol) was added dropwise to isobutylisothiocyanate (2.00 mL, 16.5 mmol) during 15 minutes at room temperature. The reaction mixture was heated to reflux for 3.5 h and the solvent was evaporated off to give the title compound (2.37 g, 98%) as a colourless oil.

¹H NMR (DMSO-d₆): δ 7.40 (s, 1H), 7.29 (s, 1H), 3.15 (broad s, 2H), 2.80 (d, 2H), 1.81 (m, 1H), 0.83 (d, 6H).

b) 6-Amino-1-isobutyl-3-methyl-5-nitroso-2-thioxo-1H-pyrimidin-4-one

A solution of cyanoacetic acid (1.52 g, 17.8 mmol) in acetic anhydride (2.45 mL, 25.9 mmol) was added to 1-isobutyl-3-methylthiourea (2.37 g, 16.2 mmol). The reaction mixture was heated to 60° C. for 1.5 h. The solvent was evaporated and the resulting red oil was redissolved in ethanol (5 mL) and 5M sodium hydroxide (1.6 mL, 8.1 mmol) was added. The reaction mixture was refluxed for 2 h. The solvent was co-evaporated with ethanol and the resulting pale brown solid was purified by flash chromatography (ethyl acetate) to yield 6-amino-1-isobutyl-3-methyl-2-thioxo-1H-pyrimidin-4-one (1.0 g, 29%) as a yellow solid.

Sodium nitrite (0.34 g, 4.9 mmol) in water (1.5 mL) was added to a solution of the amine (1.00 g, 4.7 mmol) in ethanol (7.0 mL) at room temperature. 5M Hydrochloric acid (1.0 mL, 4.9 mmol) was added and the resulting dark red reaction mixture was stirred at room temperature for 2 h. Ethanol (20 mL) was added and the red crystals were filtered off and washed with diethyl ether. Drying of the crystals gave the title compound (0.68 g, 60%).

¹H NMR (DMSO-d₆): δ 12.87 (s, 1H), 9.35 (s, 1H), 4.28 (dd, 2H), 3.75 (s, 3H), 2.34 (m, 1H), 0.90 (d, 6H).

c) 3-Isobutyl-1-methyl-2-thioxanthine

Palladium on carbon (3.70 g) was added to a solution of 6-amino-1-isobutyl-3-methyl-5-nitroso-2-thioxo-1H-pyrimidin-4-one (6.0 g, 24.8 mmol) in tetrahydrofuran (1200 mL) and water (300 mL) and the reaction mixture was hydrogenated (2.5 bar) for 21 h. The catalyst was filtered off and the tetrahydrofuran was evaporated off under reduced pressure. The residue was extracted with ethyl acetate (3×200 mL). The organic phase was concentrated and ethanol (100 mL) was added to the residue and evaporated.

The brown diamine intermediate was dissolved in triethyl orthoformate (50 mL) and the reaction mixture was heated to 140° C. for 40 minutes. The reaction mixture was concentrated and co-evaporation with ethanol afforded a brown solid. The residue was purified by flash chromatography (heptane/ethyl acetate, 2:1-ethyl acetate) followed by washing of the solid with diethyl ether and hexane to give the title compound (160 mg, 2.7%).

¹H NMR (DMSO-d₆): δ 13.86 (s, 1H), 8.21 (s, 1H), 4.34 (d, 2H, J 7.1 Hz), 3.89 (s, 3H), 2.40 (m, 1H), 0.86 (d, 6H, J 7.1 Hz).

¹³C NMR (DMSO-d₆): δ 174.68, 153.33, 148.41, 141.73, 109.92, 52.83, 37.17, 25.77, 19.92.

EXAMPLE 14

3-(2-Tetrahydrofuryl-methyl)-2-thioxanthine a) 6-Amino-1-(2-tetrahydrofuryl-methyl)-2-thioxo-2,3-dihydro-1H-pyrimidin-4-one 2-Tetrahydrofuryl-methyl-thiourea (1.0 g, 6.2 mmol) and ethyl cyanoacetate (0.85 g, 7.5 mmol) were added to a solution of sodium ethoxide [freshly made from sodium (0.16 g, 6.9 mmol) and absolute ethanol (4 mL)]. The resulting mixture was refluxed for 3.5 h. After cooling to room temperature, the solvent was evaporated under reduced pressure, and the resulting viscous syrup was re-dissolved in water (30 mL). This basic solution was neutralized with 2M hydrochloric acid. The resulting precipitate was collected by filtration and the solid was washed with water. This crude product (1.3 g, 90%) was used without further purification.

¹H NMR (DMSO-d₆): δ 11.9 (s, 1H), 6.79 (s, 2H), 4.91 (s, 1H), 4.62-4.65 (m, 1H), 4.21-4.31 (m, 3H), 3.81-3.87 (m, 1H), 3.63-3.68 (m, 1H), 1.77-2.01 (m, 3H), 1.57-1.65 (m, 1H).

MS (ES) ᵐ/z 228 (M+1).

b) 6-Amino-1-(2-tetrahydrofuryl-methyl)-5-nitroso-2-thioxo-2,3-dihydro-1H-pyrimidin-4-one 6-Amino-1-(2-tetrahydrofuryl-methyl)-2-thioxo-2,3-dihydro-1H-pyrimidin-4-one (1.3 g, 5.6 mmol) was suspended in 10% aqueous acetic acid (25 mL). Sodium nitrite (0.43 g, 6.2 mmol) was added and this mixture was heated at 75° C. for 1 h. The purple solid was collected by filtration, washed and dried, giving the title product (1.3 g, 90%).

¹H NMR: δ 13.3 (br s, 1H), 12.8 (br s, 1H), 8.93 (br s, 1H), 4.57 (br s, 1H), 4.45 (br s, 1H), 4.18-4.24 (m, 1H), 3.74-3.79 (m, 1H), 3.59-3.64 (m, 1H), 1.86-2.01 (m, 2H), 1.74-1.82 (m, 1H), 1.59-1.67 (m, 1H).

c) δ 6-Diamino-1-(2-tetrahydrofuryl-methyl-2-thioxo-2,3-dihydro-1H-pyrimidin-4-one 6-Amino-1-(2-tetrahydrofuryl-methyl)-5-nitroso-2-thioxo-2,3-dihydro-1H-pyrimidin-4-one (1.3 g, 5.1 mmol) was dissolved in 32% aqueous ammonia (15 mL) and water (15 mL) was added. The red solution was heated at 70° C. while sodium dithionite (2.2 g, 13 mmol) was added in small portions. Heating was continued for another 15 minutes and then the yellow solution was stirred at ambient temperature for 1 h. The solution was neutralized with 2M hydrochloric acid. The yellow precipitate was collected by filtration, washed with water, and dried, giving the title product (0.90 g, 73%). This material was used in the next step without further purification.

¹H NMR (DMSO-d₆): δ 5.96 (s, 2H), 4.74 (br d, 1H), 4.35 (br s, 1H), 4.21-4.28 (m, 1H), 3.84-3.89 (m, 1H), 3.64-3.69 (m, 1H), 3.49 (br s, 2H), 1.78-2.01 (m, 4H), 1.60-1.67 (1H).

MS (ES) ᵐ/z 243 (M+1).

d) 3-(2-Tetrahydrofuryl-methyl)-2-thioxanthine 5,6-Diamino-1-(2-tetrahydro furyl-methyl)-2-thioxo-2,3-dihydro-1H-pyrimidin-4-one (0.25 g, 1.0 mmol) was dissolved in formic acid (1 mL) and heated at 70° C. for 0.5 h. After a few minutes a pink solid formed in the solution. The excess of formic acid was evaporated off and the resulting solid dissolved in 10% sodium hydroxide solution (4 mL). This solution was heated at 70° C. for 40 minutes, then neutralized with 2M hydrochloric acid. The resulting precipitate was collected by filtration, washed with water and dried, giving pure product (0.23 g, 87%).

¹H NMR (DMSO-d₆): δ 13.8 (br s, 1H), 12.4 (br s, 1H), 8.16 (s, 1H), 4.53-4.61 (m, 2H), 4.38-4.44 (m, 1H), 3.79-3.84 (m, 1H), 3.58-3.63 (m, 1H), 1.72-1.98 (m, 4H).

¹³C NMR (DMSO-d₆): δ 173.65, 152.68, 149.90, 141.41, 110.96, 52.97, 35.31, 30.09, 25.88, 25.32.

MS (ES) ᵐ/z 253 (M+1).

EXAMPLE 15

3-(2-Methoxy-ethyl)-2-thioxanthine a) 6-Amino-1-(2-methoxy-ethyl)-2-thioxo-2,3-dihydro-1H-pyrimidin-4-one

The title compound was prepared in accordance with the general method of Example 14 (a) but using (2-methoxy-ethyl)-thiourea (1.5 g, 11 mmol), yielding the title compound as a white solid (2.1 g, 93%).

$^1$H NMR (DMSO-$d_6$): δ 11.9 (s, 1H), 6.82 (s, 2H), 4.89 (s, 1H), 4.53 (broad s, 2H), 3.62 (t, 2H, J=5.9 Hz), 3.29 (s, 3H).

MS (ES) $^m$/z 202 (M+1).

b) 6-Amino-1-(2-methoxy-ethyl)-5-nitroso-2-thioxo-2,3-dihydro-1H-pyrimidin-4-one 6-Amino-1-(2-methoxy-ethyl)-2-thioxo-2,3-dihydro-1H-pyrimidin-4-one (1.0 g, 5.0 mmol) was suspended in 10% acetic acid (20 mL). Sodium nitrite (0.38 g, 5.5 mmol) was added and the resulting mixture was heated at 75° C. for 1 h. The reaction mixture became first pink and then purple. Water (20 mL) was added and the reaction mixture was put in the fridge overnight. The purple solid was collected by filtration and washed with water to give the title compound (0.42 g, 37%). A second crop of product (0.22 g, 19%) was obtained by reducing the volume of the purple filtrate. The crude product was used in the following step without further purification.

$^1$H NMR (DMSO-$d_6$): δ 13.4 (br s, 1H), 12.8 (br s, 1H), 9.06 (br s, 1H), 4.54 (br s, 2H), 3.60 (t, 2H, J 5.8 Hz), 3.24 (s, 3H).

c) δ 6-Diamino-1-(2-methoxy-ethyl)-2-thioxo-2,3-dihydro-1H-pyrimidin-4-one

The title compound was prepared in accordance with the general method of Example 14 (c) but using 6-amino-1-(2-methoxy-ethyl)-5-nitroso-2-thioxo-2,3-dihydro-1H-pyrimidin-4-one (0.42 g, 1.8 mmol), yielding the title compound as a yellow solid (0.28 g, 68%).

$^1$H NMR (DMSO-$d_6$): δ 11.9 (br s, 1H), 5.94 (s, 2H), 4.58 (br s, 2H), 3.64 (t, 2H, J 5.6 Hz), 3.47 (br s, 2H), 3.28 (s, 3H).

MS (ES) $^m$/z 217 (M+1).

d) 3-(2-Methoxy-ethyl)-2-thioxanthine 5,6-Diamino-1-(2-methoxy-ethyl)-2-thioxo-2,3-dihydro-1H-pyrimidin-4-one (0.27 g, 1.3 mmol) was suspended in formic acid (2 mL) and this solution was heated at 90° C. for 1.5 h. Excess formic acid was evaporated off under reduced pressure. 10% Sodium hydroxide solution (5 mL) was added to the orange solid and the resulting solution was heated at 90° C. for 2 h. The reaction mixture was neutralized with dilute acetic acid. The resulting solution was put in the fridge for several days, then the orange needle-like crystals that had formed were collected by filtration and washed with water. Yield: (0.11 g, 40%).

$^1$H NMR (DMSO-$d_6$): δ 13.8 (broad s, 1H), 12.5 (broad s, 1H), 8.16 (s, 1H), 4.65 (t, 2H, J 6.4 Hz), 3.73 (t, 2H, J 6.4 Hz), 3.28 (s, 3H).

$^{13}$C NMR (DMSO-$d_6$): δ 172.14, 151.06, 148.02, 139.85, 109.20, 66.04, 56.65, 44.72.

MS (ES) $^m$/z 227 (M+1).

EXAMPLE 16

3-(3-(1-Morpholinyl)-propyl)-2-thioxanthine a) 6-Amino-1-(3-(1-morpholinyl)-propyl)-2-thioxo-2,3-dihydro-1H-pyrimidin-4-one The title compound was prepared in accordance with the general method of Example 14 (a) but using 1-(3-(1-morpholinyl)-propyl)-2-thiourea (1.1 g, 5.3 mmol), yielding the title compound as a white solid (1.2 g, 87%).

$^1$H NMR (DMSO-$d_6$): δ 11.8 (s, 1H), 7.24 (s, 2H), 4.84 (s, 1H), 4.33 (br s, 2H), 3.55-3.57 (m, 4H), 2.30-2.36 (m, 6H), 1.82-1.89 (m, 2H).

MS (ES) $^m$/z 271 (M+1).

c) δ 6-Diamino-1-(3-(1-morpholinyl)-propyl)-2-thioxo-2,3-dihydro-1H-pyrimidin-4-one 6-Amino-1-(3-(1-morpholinyl)-propyl)-2-thioxo-2,3-dihydro-1H-pyrimidin-4-one (0.57 g, 2.1 mmol) was dissolved in 10% acetic acid (10 mL). Sodium nitrite (0.16 g, 2.3 mmol) was added and the slurry was stirred at ambient temperature. After 2 h there was still a lot of starting material left. More sodium nitrite (0.32 g, 4.6 mmol) was added and the solution stirred overnight. The precipitate was collected by filtration and washed with water. This extremely insoluble solid was reduced without analysis. The solid was dissolved in 32% aqueous ammonia (6 mL) and then water (6 mL) was added. The resulting red solution was heated at 70° C. and sodium dithionite (0.91 g, 5.2 mmol) was added in small portions. Then the solution was stirred at 70° C. for 1.5 h. More sodium dithionite (0.91 g, 5.2 mmol) was added and the solution stirred at 70° C. for another 2.5 h. The neutral solution was filtered to remove insoluble solid. The filtrate was concentrated and the resulting yellow solid suspended in water. The solid was collected by filtration, washed with water, and dried to yield the title product (0.068 g, 11%).

$^1$H NMR: δ 12.0 (br s, 1H), 6.48 (s, 2H), 3.59 (m, 4H), 2.30-2.45 (m, 6H), 1.88-1.91 (m, 2H).

MS (ES) $^m$/z 286 (M+1).

d) 3-(3-(1-Morpholinyl)-propyl)-2-thioxanthine 5,6-Diamino-1-(3-(1-morpholinyl)-propyl)-2-thioxo-2,3-dihydro-1H-pyrimidin-4-one (0.068 g, 0.24 mmol) was dissolved in formic acid (0.4 mL) and stirred at ambient temperature for 1 h. The excess of formic acid was evaporated off and 10% sodium hydroxide solution (1.5 mL) was added and the yellow solution was heated at 70° C. for 40 minutes. The cooled solution was neutralized with 2M hydrochloric acid and put into the fridge for several hours. The precipitate was collected by filtration, washed with water, and dried yielding the title compound as an off-white solid (0.025 g, 36%).

$^1$H NMR (DMSO-$d_6$): δ 13.7 (broad s, 1H), 12.4 (s, 1H), 8.17 (s, 1H), 4.53 (t, 2H, J 7.5 Hz), 3.52 (m, 4H), 2.31-2.46 (m, 6H), 1.91-1.99 (m, 2H).

$^{13}$C NMR (DMSO-$d_6$): δ 173.68, 152.99, 149.82, 141.75, 111.24, 66.39, 55.70, 53.43, 46.58, 23.35.

MS (ES) $^m$/z 296 (M+1).

EXAMPLE 17

3-(2-Furyl-methyl)-2-thioxanthine a) 6-Amino-1-(2-furyl-methyl)-2-thioxo-2,3-dihydro-1H-pyrimidin-4-one

The title compound was prepared in accordance with the general method of Example 14 (a) except that the reaction time was reduced to 1.5 h and the product was precipitated with dilute acetic acid. Using 2-furyl-methylthiourea (1.0 g, 6.4 mmol), the title product (0.95 g, 66%) was obtained.

$^1$H NMR (DMSO-$d_6$): δ 11.8 (br s, 1H), 7.58-7.62 (m, 1H), 7.05 (br s, 2H), 6.38-6.42 (m, 1H), 6.31-6.36 (m, 1H), 5.68 (br s, 2H), 4.85 (s, 1H).

MS (ES) $^m/z$ 224 (M+1).

b) 6-Amino-1-(2-furyl-methyl)-5-nitroso-2-thioxo-2,3-dihydro-1H-pyrimidin-4-one The title compound was prepared in accordance with the general method of Example 14 (b) except that the reaction mixture was first heated at 60° C. for 1 h and then stirred at ambient temperature for 1 h. The product (0.25 g, 60%) was obtained as a brown solid when 6-amino-1-(2-furyl-methyl)-2-thioxo-2,3-dihydro-1H-pyrimidin-4-one (0.37 g, 1.6 mmol) and 2 equivalents of sodium nitrite (0.23 g, 3.3 mmol) were used.

$^1$H NMR: δ 12.1 (br s, 1H), 7.54-7.57 (m, 1H), 7.45-7.47 (m, 1H), 6.37-6.40 (m, 1H), 6.32-6.38 (m, 1H), 6.30-6.32 (m, 1H), 5.62 (s, 2H), 5.48 (s, 2H).

c) δ 6-Diamino-1-(2-furyl-methyl)-2-thioxo-2,3-dihydro-1H-pyrimidin-4-one

The title compound (0.12 g, 52%) was prepared in accordance with the general method in Example 14 (c) starting from 6-amino-1-(2-furyl-methyl)-5-nitroso-2-thioxo-2,3-dihydro-1H-pyrimidin-4-one (0.25 g, 0.99 mmol), and was used without purification in the next step.

$^1$H NMR (DMSO-$d_6$): δ 12.5 (br s, 1H), 12.2 (s, 1H), 7.58-7.60 (m, 1H), 7.55-7.57 (m, 1H), 6.38-6.41 (m, 2H), 6.34-6.37 (m, 1H), 6.30 (br s, 2H), 5.77 (s, 2H), 5.63 (s, 2H).

MS (ES) $^m/z$ 239 (M+1).

d) 3-(2-Furyl-methyl)-2-thioxanthine 5,6-Diamino-1-(2-furyl-methyl)-2-thioxo-2,3-dihydro-1H-pyrimidin-4-one (0.12 g, 0.51 mmol) in formic acid (0.5 mL) was stirred at ambient temperature for 0.5 h. The excess of formic acid was evaporated off and the resulting solid dissolved in 10% sodium hydroxide solution (3 mL). This solution was heated at 70° C. for 0.5 h. The reaction mixture was neutralized with 2M hydrochloric acid. The resulting precipitate was collected by filtration, washed with water, and dried. Yield: (0.047 g, 37%).

$^1$H NMR (DMSO-$d_6$): δ 13.9 (s, 1H), 12.5 (s, 1H), 8.18 (s, 1H), 7.55-7.57 (m, 1H), 6.36-6.39 (m, 2H), 5.69 (s, 2H).

$^{13}$C NMR (DMSO-$d_6$): δ 174.14, 152.85, 149.56, 149.33, 142.77, 141.80, 110.93, 109.40, 44.26.

MS (ES) $^m/z$ 249 (M+1).

EXAMPLE 18

3-(4-Methoxybenzyl)-2-thioxanthine a) 6-Amino-1-(4-methoxybenzyl)-2-thioxo-2,3-dihydro-1H-pyrimidin-4-one

The title compound was prepared according to the general method of Example 14 (a) except that the reaction was conducted for 2.5 h at reflux temperature followed by 16 h at ambient temperature and precipitation of the product was made using dilute acetic acid. Starting with (4-methoxybenzyl)-thiourea (1.0 g, 5.1 mmol) afforded the desired product. (1.2 g, 92%).

$^1$H NMR (CD$_3$OD): δ 7.19 (d, 2H, J 8.6 Hz), 6.89 (d, 2H, J 8.6 Hz), 5.72 (br s, 2H), 5.06 (s, 1H), 3.77 (s, 3H).

MS (ES) $^m/z$ 264 (M+1).

b) 6-Amino-1-(4-methoxybenzyl)-5-nitroso-2-thioxo-2,3-dihydro-1H-pyrimidin-4-one The title compound was prepared according to the general method of Example 14 (b) but using a 2.5 h reaction time. Using 6-amino-1-(4-methoxybenzyl)-2-thioxo-2,3-dihydro-1H-pyrimidin-4-one (1.2 g, 4.7 mmol) yielded the product (1.2 g, 88%) as a blue-green solid that was used in the subsequent reaction without further purification.

$^1$H NMR (DMSO-$d_6$): δ 11.9 (s, 1H), 7.18-7.12 (m, 2H), 6.95-6.83 (m, 2H), 5.58 (br s, 2H), 3.70 (s, 3H).

c) δ 6-Diamino-1-(4-methoxybenzyl)-2-thioxo-2,3-dihydro-1H-pyrimidin-4-one

The title compound was prepared according to the general method of Example 14 (c) except that dilute acetic acid was used for neutralization of the reaction mixture. The desired product (0.83 g, 73%) was prepared as a yellow solid starting from 6-amino-1-(4-methoxybenzyl)-5-nitroso-2-thioxo-2,3-dihydro-1H-pyrimidin-4-one (1.2 g, 4.1 mmol).

$^1$H NMR (DMSO-$d_6$): δ 11.7 (br s, 2H), 7.20-7.12 (br s, 2H), 6.92-6.85 (m, 2H), 6.06 (s, 2H), 5.73 (br s, 2H), 3.71 (s, 3H).

MS (ES) $^m/z$ 279 (M+1).

d) 3-(4-Methoxybenzyl)-2-thioxanthine 5,6-Diamino-1-(4-methoxybenzyl)-2-thioxo-2,3-dihydro-1H-pyrimidin-4-one (0.83 g, 3.0 mmol) was dissolved in formic acid (3.0 mL) and the resulting solution heated at 100° C. for 1 h. The excess formic acid was removed under reduced pressure and the residue dissolved in 10% potassium hydroxide solution (8 mL) and heated at 100° C. for 15 minutes. The reaction mixture was neutralized with 10% acetic acid and the resulting precipitate collected by filtration. The precipitate was recrystallised from ethanol: dimethylformamide and the isolated crystals dissolved in 1M potassium hydroxide solution, precipitated by neutralization with 10% acetic acid and collected by filtration. After drying, the title compound (0.14 g, 16%) was obtained.

$^1$H NMR (DMSO-$d_6$): δ 13.9 (br s, 1H), 12.5 (s, 1H), 8.15 (s, 1H), 7.36 (d, 2H, J 8.6 Hz), 6.84 (d, 2H, J 8.9 Hz), 5.63 (s, 2H), 3.70 (s, 3H).

$^{13}$C NMR (DMSO-$d_6$): δ 173.85, 158.52, 152.45, 149.36, 141.41, 129.35, 127.97, 113.58, 110.83, 55.01, 49.63.

MS (ES) $^m/z$ 289 (M+1).

EXAMPLE 19

3-(4-Fluorobenzyl)-2-thioxanthine a) 6-Amino-1-(4-fluorobenzyl)-2-thioxo-2,3-dihydro-1H-pyrimidin-4-one

The title compound was prepared according to the general method of Example 14 (a) except that the reaction time was 16 h and precipitation of the product was made by treatment with dilute acetic acid. (4-Fluorobenzyl)-thiourea (1.0 g, 5.4 mmol) afforded the product (1.2 g, 86%) as a white solid.

$^1$H NMR (DMSO-$d_6$): δ 11.9 (br s, 1H), 7.27-7.11 (m, 4H), 6.91 (s, 2H), 5.67 (br s, 2H), 4.89 (s, 1H).

MS (ES) $^m$/z 252 (M+1).

b) 6-Amino-1-(4-fluorobenzyl)-5-nitroso-2-thioxo-2,3-dihydro-1H-pyrimidin-4-one The title compound was prepared according to the general method of Example 14 (b) except increasing the reaction time to a total of 8 h. 6-Amino-1-(4-fluorobenzyl)-2-thioxo-2,3-dihydro-1H-pyrimidin-4-one (1.2 g, 4.7 mmol) afforded the desired product (0.88 g, 67%).

$^1$H NMR (DMSO-$d_6$): δ 13.1 (br s, 1H), 12.8 (br s, 1H), 7.33-7.08 (m, 2H), 7.13 (t, 2H, J 8.7 Hz), 5.62 (br s, 2H).

c) δ 6-Diamino-1-(4-fluorobenzyl)-2-thioxo-2,3-dihydro-1H-pyrimidin-4-one

The title compound was prepared in accordance with the general method of Example 14 (c) except that the reaction was kept at 75° C. for 1 h followed by 20 minutes at ambient temperature and neutralization of the reaction mixture was made with dilute acetic acid. Using 6-amino-1-(4-fluorobenzyl)-5-nitroso-2-thioxo-2,3-dihydro-1H-pyrimidin-4-one (0.88 g, 3.1 mmol) gave the desired product (0.55 g, 66%).

$^1$H NMR (DMSO-$d_6$): δ 12.1 (br s, 2H), 7.29-7.12 (m, 4H), 6.08 (s, 2H), 5.75 (br s, 2H).

MS (ES) $^m$/z 267 (M+1).

d) 3-(4-Fluoro-benzyl)-2-thioxanthine

The title compound was prepared in accordance with the general method of Example 18 (d) but using 5,6-diamino-1-(4-fluorobenzyl)-2-thioxo-2,3-dihydro-1H-pyrimidin-4-one (0.55 g, 2.1 mmol), yielding the desired product (0.24 g, 41%).

$^1$H NMR (DMSO-$d_6$): δ 13.9 (br s, 1H), 12.5 (s, 1H), 8.15 (s, 1H), 7.44 (dd, 2H, J 8.6, 8.6 Hz), 7.12 (t, 2H, J 8.9 Hz), 5.68 (s, 2H).

$^{13}$C NMR (DMSO-$d_6$): δ 173.96, 160.14, 152.48, 149.28, 141.44, 132.19, 129.83 (d, J 8.0 Hz), 115.00 (d, J 22 Hz), 110.82, 49.49.

MS (ES) $^m$/z 277 (M+1).

EXAMPLE 20

3-Phenethyl-2-thioxanthine a) 6-Amino-1-phenethyl-2-thioxo-2,3-dihydro-1H-pyrimidin-4-one

The title compound was prepared according to the general method of Example 14 (a) apart from a 3.5 h reaction time at reflux followed by reaction at ambient temperature for 16 h. The product was precipitated by treatment with dilute acetic acid. Phenethylthiourea (1.0 g, 5.6 mmol) afforded the product (1.3 g, 95%) as a white solid.

$^1$H NMR (DMSO-$d_6$): δ 11.8 (br s, 1H), 7.37 (d, 2H, J 7.1 Hz), 7.31 (t, 2H, J 7.4 Hz), 7.22 (t, 1H, J 7.2 Hz), 7.08 (br s, 2H), 4.88 (s, 2H), 4.52 (br s, 1H), 3.32 (br s, 1H), 2.92 (t, 2H, J 8.3 Hz).

MS (ES) $^m$/z 248 (M+1).

b) 6-Amino-5-nitroso-1-phenethyl-2-thioxo-2,3-dihydro-1H-pyrimidin-4-one

The title compound was prepared according to the general method of Example 14 (b) except increasing the reaction time to 1.5 h. 6-Amino-1-phenethyl-2-thioxo-2,3-dihydro-1H-pyrimidin-4-one (1.3 g, 5.3 mmol) afforded the desired product (1.3 g, 92%).

$^1$H NMR (DMSO-$d_6$): δ 13.5 (br s, 1H), 12.8 (br s, 1H), 9.34 (br s, 1H), 7.37-7.28 (m, 4H), 7.25-7.20 (m, 1H), 4.55 (br s, 2H), 2.90 (t, 2H, J 8.4 Hz).

c) 5,6-Diamino-1-phenethyl-2-thioxo-2,3-dihydro-1H-pyrimidin-4-one

The title compound was prepared in accordance with the general method of Example 14 (c) except that the reaction was kept at 75° C. for 15 minutes followed by 1 h and 20 minutes at ambient temperature and neutralization of the reaction mixture was made with dilute acetic acid. Using 6-amino-5-nitroso-1-phenethyl-2-thioxo-2,3-dihydro-1H-pyrimidin-4-one (1.3 g, 4.8 mmol) the desired product (1.1 g, 88%) was isolated.

$^1$H NMR (DMSO-$d_6$): δ 10.1 (br s, 2H), 7.46-7.16 (m, 5H), 6.25 (s, 2H), 4.56 (br s, 2H), 2.94 (t, 2H, J 8.3 Hz).

MS (ES) $^m$/z 263 (M+1).

d) 3-Phenethyl-2-thioxanthine

The title compound was prepared in accordance with the general method of Example 18 (d) with the exception that for the final neutralization 1M hydrochloric acid was utilized. Using 5,6-diamino-1-phenethyl-2-thioxo-2,3-dihydro-1H-pyrimidin-4-one (0.55 g, 2.1 mmol) yielded the desired product (0.39 g, 34%).

$^1$H NMR (DMSO-$d_6$): δ 7.53 (s, 1H), 7.32 (d, 4H, J 4.5 Hz), 7.22 (m, 1H), 4.63 (m, 2H), 3.01 (m, 2H), 1.88 br s, 2H).

$^{13}$C NMR (DMSO-$d_6$): δ 170.56, 155.20, 150.51, 146.41, 138.54, 128.58, 128.46, 126.34, 117.49, 48.82, 32.59.

MS (ES) $^m$/z 273 (M+1).

EXAMPLE 21

Enantiomers of 3-(2-Tetrahydrofuryl-methyl)-2-thioxanthine

A solution of racemic 3-(2-tetrahydrofuryl-methyl)-2-thioxanthine (3 mg/mL) was separated by chiral HPLC on a Chiralpak AD-RH column (4.6×150 mm; 5 μm). The mobile phase was methanol:acetic acid:triethylamine (100:0.1:0.1) and the flow rate 1 mL/min. The injection volume was 20 μL.

Enantiomer 1 e.e. 93.6%; MS (ES) $^m$/z 253 (M+1).

Enantiomer 2 e.e. 97.3%; MS (ES) $^m$/z 253 (M+1).

EXAMPLE 22

3-n-Butyl-2-thioxanthine

The title compound was prepared using the procedure described for Example 6.

$^1$H NMR (DMSO-$d_6$): δ 13.82 (s, 1H), 12.40 (s, 1H), 8.15 (s, 1H), 4.45 (m, 2H), 1.73 (m, 2H), 1.34 (sextet, 2H, J=7.5), 0.92 (t, 3H, J=7.5).

$^{13}$C NMR (DMSO-$d_6$): δ 173.31, 152.62, 149.30, 141.47, 110.84, 47.37, 28.61, 19.48, 13.72.

MS (ES) $m$/z 225 (M+1).

Screens

Methods for the determination of MPO inhibitory activity are disclosed in co-pending patent application WO 02/090575. The pharmacological activity of compounds according to the invention was tested in the following screen:

Assay buffer: 20 mM sodium/potassium phosphate buffer pH 6.5 containing 10 mM taurine and 100 mM NaCl.

Developing reagent: 2 mM 3,3',5,5'-tetramethylbenzidine (TMB), 200 µM KI, 200 mM acetate buffer pH 5.4 with 20% DMF.

To 10 µl of diluted compounds in assay buffer, 40 µl of human MPO (final concentration 2.5 nM) was added for 10 minutes at room temperature. Then 50 µl of $H_2O_2$ (final concentration 100 µM), or assay buffer alone as a control, were added for 10 minutes at room temperature. The reaction was stopped by adding 10 µl 0.2 mg/ml of catalase (final concentration 18 µg/ml) for 5 minutes before 100 µl of TMB developing reagent was added (2 mM TMB in 200 mM acetate buffer pH 5.4 containing 20% dimethylformamide (DMF) and 200 µM KI). Plates were mixed and the amount of oxidised 3,3',5,5'-tetramethylbenzidine formed was then measured after about 5 minutes using absorbance spectroscopy at about 650 nM. $IC_{50}$ values were then determined using standard procedures.

When tested in the above screen, the compounds of Examples 1 to 22 gave $IC_{50}$ values of less than 60 µM, indicating that they are expected to show useful therapeutic activity. Representative results are shown in the following Table:

| Compound | Inhibition of MPO ($IC_{50}$ µM) |
| --- | --- |
| Example 6 | 0.87 |
| Example 10 | 0.53 |
| Example 14 | 0.51 |
| Example 15 | 0.44 |
| Example 16 | 2.94 |
| Example 17 | 7.57 |
| Example 18 | 0.49 |
| Example 20 | 0.96 |

The invention claimed is:

1. A compound of the following formula

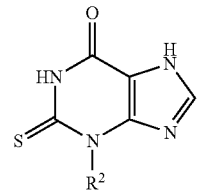

wherein $R^2$ represents ($C_1$-$C_6$) alkyl substituted by ($C_1$-$C_6$) alkoxy, or a pharmaceutically acceptable salt thereof.

* * * * *